(12) United States Patent
Tuthill

(10) Patent No.: US 8,716,012 B2
(45) Date of Patent: May 6, 2014

(54) ALPHA THYMOSIN PEPTIDES AS VACCINE ENHANCERS

(75) Inventor: Cynthia W. Tuthill, Menlo Park, CA (US)

(73) Assignee: Sciclone Pharmaceuticals, Inc., Foster City, CA (US)

( * ) Notice: Subject to any disclaimer, the term of this patent is extended or adjusted under 35 U.S.C. 154(b) by 515 days.

(21) Appl. No.: 12/776,976

(22) Filed: May 10, 2010

(65) Prior Publication Data

US 2010/0285060 A1 Nov. 11, 2010

Related U.S. Application Data

(60) Provisional application No. 61/323,155, filed on Apr. 12, 2010, provisional application No. 61/176,625, filed on May 8, 2009, provisional application No. 61/237,932, filed on Aug. 28, 2009.

(51) Int. Cl.
*A61K 39/00* (2006.01)
*C12N 15/00* (2006.01)
*A61K 38/22* (2006.01)

(52) U.S. Cl.
USPC ............... 435/320.1; 514/12.9; 424/184.1

(58) Field of Classification Search
None
See application file for complete search history.

(56) References Cited

U.S. PATENT DOCUMENTS

| | | |
|---|---|---|
| 4,077,949 A | 3/1978 | Goldstein |
| 4,079,127 A | 3/1978 | Goldstein et al. |
| 4,079,137 A | 3/1978 | Cyrus et al. |
| 4,293,455 A | 10/1981 | Merrifield et al. |
| 4,361,673 A | 11/1982 | McGregor |
| 4,444,757 A | 4/1984 | Strausser |
| 4,560,676 A | 12/1985 | Merrifield |
| 4,612,365 A | 9/1986 | Birr et al. |
| 4,910,296 A | 3/1990 | Birr et al. |
| 5,308,833 A | 5/1994 | Scharschmidt et al. |
| 5,432,165 A | 7/1995 | Adair et al. |
| 5,468,729 A | 11/1995 | Chretien et al. |
| 5,620,896 A | 4/1997 | Herrmann et al. |

(Continued)

FOREIGN PATENT DOCUMENTS

| | | |
|---|---|---|
| AU | 2002363248 | 11/2007 |
| EP | 0603305 | 5/1997 |

(Continued)

OTHER PUBLICATIONS

Rongzhong, et al. Safety and Immunogenicity of H5N1 Influenza Vaccine Based on Baculovirus Surface Display System of *Bombyx mori*. PLoS One. 2008; 3(12): e3933-1-7.*

(Continued)

*Primary Examiner* — Zachariah Lucas
*Assistant Examiner* — Stuart W Snyder
(74) *Attorney, Agent, or Firm* — Cooley LLP

(57) ABSTRACT

The present invention provides methods of vaccination as well as pharmaceutical combinations and kits for enhancing vaccine effectiveness, including for immunodeficient or immunecompromised patients, including non-responders and low-responders to vaccination. As disclosed herein, the invention relates to administering a vaccine and a regimen of thymosin alpha peptide so as to provide higher antibody titers, speed the development of such antibody titers, and/or to provide for a longer duration of such antibody titers, thereby providing a greater protective effect. In another aspect, the invention allows for reducing a vaccine dose, such as an influenza vaccine dose, by administration of a thymosin peptide regimen.

33 Claims, 25 Drawing Sheets

(56) References Cited

U.S. PATENT DOCUMENTS

| | | | |
|---|---|---|---|
| 5,632,983 | A | 5/1997 | Hadden |
| 5,750,501 | A | 5/1998 | Chretien et al. |
| 5,849,696 | A | 12/1998 | Chretien et al. |
| 5,888,980 | A | 3/1999 | Ripka et al. |
| 5,939,423 | A | 8/1999 | Karlin et al. |
| 6,001,799 | A | 12/1999 | Chretien et al. |
| 6,106,868 | A | 8/2000 | Mutchnick |
| 6,172,046 | B1 | 1/2001 | Albrecht |
| 6,200,952 | B1 | 3/2001 | Horwitz |
| 6,288,033 | B1 | 9/2001 | Leung |
| 6,495,521 | B2 | 12/2002 | Horwitz |
| 7,208,167 | B2 | 4/2007 | Rudolph |
| 7,297,676 | B2 * | 11/2007 | Rudolph et al. ......... 424/195.11 |
| 2003/0124136 | A1 | 7/2003 | Hadden |
| 2003/0185799 | A1 | 10/2003 | Rudolph |
| 2005/0020495 | A1 | 1/2005 | Martins |
| 2005/0049191 | A1 | 3/2005 | Rudolph et al. |
| 2005/0054845 | A1 | 3/2005 | Wands |
| 2007/0036744 | A1 | 2/2007 | Rudolph et al. |
| 2007/0048281 | A1 | 3/2007 | Maertens et al. |
| 2008/0187556 | A1 | 8/2008 | Sun et al. |
| 2009/0155260 | A1 | 6/2009 | Romani et al. |
| 2009/0275508 | A1 | 11/2009 | Romani et al. |
| 2010/0092499 | A1 | 4/2010 | Moviglia et al. |
| 2010/0221274 | A1 | 9/2010 | Rudolph et al. |
| 2010/0311656 | A1 | 12/2010 | Rudolph et al. |
| 2010/0317583 | A1 | 12/2010 | Rios et al. |

FOREIGN PATENT DOCUMENTS

| | | |
|---|---|---|
| EP | 0687181 | 8/2001 |
| WO | WO 93/05806 | 4/1993 |
| WO | WO 94/01125 | 1/1994 |
| WO | WO 94/13314 | 6/1994 |
| WO | WO 94/20131 | 9/1994 |
| WO | WO 95/12405 | 5/1995 |
| WO | WO 96/15800 | 5/1996 |
| WO | WO 98/46256 | 10/1998 |
| WO | WO 99/15194 | 4/1999 |
| WO | WO 99/59621 | 11/1999 |
| WO | WO 99/64016 | 12/1999 |
| WO | WO 00/18417 | 4/2000 |
| WO | WO 02/11749 | 2/2002 |
| WO | WO 03/035010 | 5/2003 |
| WO | WO 03/037366 | 5/2003 |
| WO | WO 2006/062917 | 6/2006 |

OTHER PUBLICATIONS

Gravenstein, et al. Augmentation of influenza antibody response in elderly men by thymosin alpha one. A double-blind placebo-controlled clinical study. Journal of the American Geriatrics Society. 1989; 37(1): 1-8. Abstract Only.*
S.B. Hall. http://www.halls.md/chart/men-weight-w.htm; downloaded Oct. 1, 2012 by sws.*
S.B. Hall. http://www.halls.md/chart/men-height-w.htm; downloaded Oct. 1, 2012 by sws.*
GlobalRPh (http://www.globalrph.com/bsa2.cgi) downloaded Oct. 1, 2012 by sws.*
Denis, et al. Development of a universal influenza A vaccine based on the M2e peptide fused to the papaya mosaic virus (PapMV) vaccine platform. Vaccine. 2008; 26: 3395-3403.*
Cronly-Dillon, Sujatha. The Effect of Preadministration of Corynebacterium parvum on the Protection Afforded by Heat-Killed and Acetone-Killed Vaccines against Experimental Mouse Typhoid. The Journal of Hygiene. 1974; 72(1): 13-18.*
Shen, et al. Recombinant Listeria monocytogenes as a live vaccine vehicle for the induction of protective anti-viral cell-mediated immunity. Proc. Natl. Acad. Sci. USA. 1995; 92: 3987-3991.*
Collins Vaccines and Cell-Mediated Immunity. Bacteriological Reviews. 1974; 38(4): 371-402.*

McConnell, et al. "The Gerontologist" 29:188A, 1989.
Ancell, C. D. et al., "Thymosin alpha-1," Am. J. Health-Syst. Pharm., 58:879-888 (2001).
Andreone, P. et al., "In vitro effect of thymosin-alpha1 and interferon-alpha on Th1 and Th2 cytokine synthesis in patients with chronic hepatitis C," Journal of Viral Hepatitis, 8(3):194-201 (2001).
Moviglia, G. A. et al., "Dendritic cell vaccine for metastatic breast cancer. Phase VII study," Abstract Book of the 29th ESMO Congress, Annals of Oncology, 15(3):iii40 (2004), Vienna, Austria, 2 pages.
Baxevanis, C. N. et al., "Enhancement of human T lymphocyte function by prothymosin $\alpha$: Increased production of interleukin-2 and expression of interleukin-2 receptors in normal human peripheral blood T lymphocytes," Immunopharmacology and Immunotoxicology, 12(4): 595-617 (1990).
Baxevanis, C. N. et al., "Immunoregulatory effects of fraction 5 thymus peptides. I. Thymosin $\alpha 1$ enhances while thymosin $\beta 4$ supresses the human autologous and allogeneic mixed lymphocyte reaction," Immunopharmacology, 13(2)133-141 (1987).
Berzofsky, J. A. et al., "Progress on new vaccine strategies against chronic viral infections," Journal of Clinical Investigation, 114(4):450-462 (2004).
Beuth, J. et al., "Thymosin $\alpha_1$ application augments immune response and down-regulates tumor weight and organ colonization in BALB/c-mice," Cancer Letters, 159(1):9-13 (2000).
Billich, A., "Thymosin $\alpha 1$: SciClone Pharmaceuticals," Curr. Opin. Investig. Drugs, 3(5):698-707 (2002).
Bistoni, F. et al., "Increase of mouse resistance to Candida albicans infection by thymosin alpha 1," Infection and Immunity, 36(2):609-614 (1982).
Chadwick, D. et al., "A pilot study of the safety and efficacy of thymosin $\alpha 1$ in augmenting immune reconstitution in HIV-infected patients with low CD4 counts taking highly active antiretroviral therapy," Clin. Exp. Immunol., 134(3):477-481 (2003).
Chan, H. L. Y. et al., "The efficacy of thymosin in the treatment of chronic hepatitis B virus infection: A meta-analysis," Aliment. Pharmacol. Ther., 15(12):1899-1905 (2001).
Chan, H. L. et al., "Thymosin-$\alpha 1$ for the treatment of chronic hepatitis B virus (HBV) infection: a meta-analysis," Digestive Disease Week, Atlanta, Georgia, Abstract 2910 (2001), 1 page.
Cordero, O. J. et al., "Prothymosin $\alpha$ enhances human natural killer cell cytotoxicity: Role in mediating signals for NK activity," Lymphokine and Cytokine Research, 11(5):277-285 (1992).
D'Agostini, C. et al., "Efficacy of combination therapy with amantadine, thymosin $\alpha 1$ and $\alpha/\beta$ interferon in mice infected with influenza A virus," Int. J. Immunopharmac, 13(2):95-102 (1996).
De Man, R. A. et al., "New developments in antiviral therapy for chronic hepatitis B infection", Scand. J. Gastroenterol., 30(212):100-104 (1995).
Di Francesco, P. et al., "Combined effect of fluconazole and thymosin $\alpha 1$ on systemic candidiasis in mice immunosuppressed by morphine treatments," Clin. Exp. Immunol., 97:347-352 (1994).
Eichberg, J. W. et al., "Effect of thymosin immunostimulation with and without corticosteroid immunosuppression on chimpanzee hepatitis B carriers," Chemical Abstracts, 106(15):487-488 (1987).
Ershler, W. B. et al., "Thymosin alpha 1 as an adjunct to influenza vaccination in the elderly: rationale and trial summaries," Ann. N. Y. Acad. Sci., 1112:375-384 (2007).
Expt. No. NIAS-153, 2G. Effect of s.c. Treatment with Thymosin Alpha-1 (ARB 06-000954) on Inhibition of SARS-CoV Replicaiton in Mice, Jun. 26, 2006, 4 pages.
Fan, G. R. et al., "Clinical Application and Perspective of Thymosin Alpha 1 in the Treatment of Viral Hepatitis," Liver disease research institute, Beijing PLA General Hospital (Beijing 100700).
Favilli, C. et al., "Modulation of natural killer activity by thymosin alpha 1 and interferon," Cancer Immunol. Immunother., 20(3):189-192 (1985).
Foon, K. A., "Biological response modifiers: the new immunotherapy," Cancer Research, 49:1621-1639 (1989).
Fujii, T. et al., "Current concepts in SARS treatment," J Infect. Chemother, 10:1-7 (2004).
Garaci, E. et al., "Effect of thymosin alpha-1 and interferon-alpha associated with zidovudine in HIV-serpositive patients," International Conference AIDS, 7(2):219 (Jun. 16-21, 1991), 1 page.

(56) References Cited

OTHER PUBLICATIONS

Garaci, E. et al., "Thymosin alpha1: From Bench to Bedside," Annals of the New York Academy of Science, 1112:225-234 (2007).
Garaci, E. et al., "Combined therapy with zidovudine, thymosin α1 and α-interferon in the treatment of HIV-infected patients," In: Combination Therapies 2. Biological Response Modifiers in the Treatment of Cancer and Infectious Diseases, Garaci, E. and Goldstein, A. L. (eds.), Plenum Press, pp. 235-242 (1993).
Garaci, E., "Thymosin Alpha 1: A Historical Overview," Annals of the New York Academy of Science, 1112:14-20 (2007).
Goldstein, A. L. et al., "From lab to bedside: emerging clinical applications of thymosin $α_1$," Expert Opinion Biol. Ther., 9(5):593-608 (2009).
Goldstein, A. L., "Clinical applications of thymosin alpha-1," Cancer Investigation, 12(5):545-547 (1994).
Goldstein, A. L. et al., "Immunologic reconstitution of patients with primary immunodeficiency diseases and cancer after treatment with thymosin," Transplantation Proceedings, 9(1):1141-1144 (1977).
Goldstein, A. L. et al., "Purification and biological activity of thymosin, a hormone of the thymus gland," Proc. Nat'l Acad. Sci. (USA), 69(7):1800-1803 (1972).
Goldstein, A. L. et al., "Thymosin α1: Isolation and sequence analysis of an immunologically active thymic polypeptide," Proc. Natl. Acad. Sci, USA, 74(2): 725-729 (1977).
Han, Y. et al., "Experience of successful recovery of one case of an elderly severe SARS patient," Chin Crit Care Med., 16(1):1-3 (2004).
Hegarty, J. E. et al., "Controlled trial of a thymic hormone extract (Thymostimulin) in 'autoimmune' chronic active hepatitis," Gut, 25:279-283 (1984).
Holmes, K. V., "SARS coronavirus: a new challenge for prevention and therapy," The Journal of Clinical Investigation, 111(11):1605-1609 (2003).
Hong, J. H. et al., "Current status of anti-HBV chemotherapy," Archives of Pharmacal Research, 21(2):89-105 (1998).
Hsia, J. et al., "Aspirin and thymosin increase interleukin-2 and interferon-production by human peripheral blood lymphocytes," Immunopharm., 17:167-173 (1989).
Huang, Y. et al., "The modulation of thymosin alpha 1 in the maturation, differentiation and function of murine bone marrow-derived dendritic cells in the absence or presence of tumor necrosis factor-alpha," International Immunopharmacology, 4:539-546 (2004).
Ishitsuka, H. et al., "Protective activity of thymosin alpha I against tumor progression in immunosuppressed mice," In: Biological Response Modifiers in Human Oncology and Immunology, Klein, T. et al. (eds.), Plenum Press, pp. 89-100 (1983).
Ishitsuka, H. et al., "Protective activity of thymosin against opportunistic infections in animal models," Cancer Immunology Immunotheraphy, 14(3):145-150 (1983).
Ishitsuka, H. et al., "Efficacy of thymosin $α_1$ in animal models," Thymic Hormones and Lymphokines, PAP. Annu. Symp. Health Sci., 3rd, pp. 425-438, New York, NY, USA (1984).
Knutsen, A. P. et al., "Thymosin-$α_1$ stimulates maturation of $CD34^+$ stem cells into $CD3^+4^+$ cells in an in vitro thymic epithelia organ coculture model," International Journal of Immunopharmacology, 21(1):15-26 (1999).
Kouttab, N. M. et al., "Production of human B and T cell growth factors is enhanced by thymic hormones," Immunopharmacology, 16(2):97-105 (1988).
Leichtling, K. D. et al., "Thymosin alpha 1 modulates the expression of high affinity interleukin-2 receptors on normal human lymphocytes," International Journal of Immunopharmacology, 12(1):19-29 (1990).
Liang, T. J. et al., "Pathogenesis, natural history, treatment, and prevention of hepatitis C," Annals of Internal Medicine, 132(4):296-305 (2000).
Low, T. L. K. et al., "The chemistry and biology of thymosin," The Journal of Biological Chemistry, 254(3)981-986 (1979).
Marshall, G. D. et al., "In vivo generation of suppressor T cells by thymosin in congenitally athymic nude mice," The Journal of Immunology, 126(2):741-744 (1981).

McConnell, L. T., "Influenza vaccine & adjuvant thymosin alpha-1. A double-blind placebo-controlled trial," Trial Analysis and Report, The George Washington University Ambulatory Care Center, Division of Geriatric Medicine (1990), 24 pages.
Mutchnick, M. G. et al., "Thymosin treatment of chronic active Hepatitis B (CAHB): Results of a pilot study," Hepatology, 10(4):575 (1989).
Mutchnick, M. G. et al., "Thymosin treatment of chronic active Hepatitis B (CAHB): A preliminary report on a controlled, double blind study," Hepatology, 8(5):1270 (1988).
Mutchnick, M. G. et al., "Thymosin treatment of chronic Hepatitis B: A placebo-controlled pilot trial," Hepatology, 14(3):409-415 (1991).
Mutchnick, M. G. et al., "Sustained response to thymosin therapy in patients with chronic Hepatitis B," Hepatology, vol. 16(4), Pt. 2, p. 66A (1992).
Mutchnick, M. G. et al., "Thymosin: An innovative approach to the treatment of chronic Hepatitis B," Combination Therapies, Plenum Press New York, pp. 149-157 (1992).
Naylor, P. H., "Zadaxin (thymosin alpha 1) for the treatment of viral hepatitis," Expert Opinion on Investigational Drugs, 8(3):281-287 (1999).
Naylor, P. H. et al., "T cell targeted immune enhancement yields effective T cell adjuvants," Intl Immunopharmacol., 3(8):1205-1215 (2003).
O'Brien, C. J. et al., "In vitro effect of TP-1 (A calf thymic extract) on suppressor t-cell function of patients with autoimmune chronic active hepatitis," Int. J. Immnopharmac., 10(6):651-656 (1988).
Ohmori, H. et al., "Restoration of immunocyte functions by thymosin alpha 1 in cyclophosphamide-induced immunodeficient mice," Immunopharmacology and Immunotoxicology, 23(1):75-82 (2001).
Ohta, Y. et al., "Immunomodulating activity of thymosin fraction 5 and thymosin $α_1$ in immunosuppressed mice," Cancer Immunol. Immunother., 15(2):108-113 (1983).
Ohta, Y. et al., "Thymosin alpha 1 enhances haematopoietic colony formation by stimulating the production of interleukin 3 in nu/nu mice," Int. J. Immunopharmacol., 8(7):773-779 (1986).
Pollack, A., "The SARS Epidemic: Treatment," The New York Times, May 6, 2003, 1 page.
Pozo, D. et al., "Thymosin α1 Interacts with the VIP receptor-effector system in rat and mouse immunocompetent cells," Immunopharmacology, 34:113-123 (1996).
Ramachandran, R. et al., "Polyethylene Glycol-Modified Interleukin-2 and Thymosin Alpha 1 in Human Immunodeficiency Virus Type 1 Infection," J. Infect. Dis., 173(4):1005-1008 (1996).
Romani, L. et al., "Thymosin α 1 activates dendritic cells for antifungal Th1 resistance through toll-like receptor signaling," Blood, 103(11):4232-4239 (2004).
Romani, L. et al., "Thymosin alpha 1: An Endogenous Regulator of Inflammation, Immunity, and Tolerance," Ann. N. Y. Acad. Sci., 1112:326-338 (2007).
Rost, K. L. et al., "Pharmacokinetics of thymosin α1 after subcutaneous injection of three different formulations in healthy volunteers," Int. J. of Clin. Pharmacol. and Therapeutics, 37(1):51-57 (1999).
Schulof, R. S. et al., "Phase I/II trial of thymosin fraction 5 and thymosin alpha one in HTLV-III seropositive subjects," Journal of Biological Response Modifiers, 5(5):429-443 (1986).
SciClone Press Release, "SciClone and Sigma-Tau Announce Positive Preliminary Results in Clinical Study Examining Zadaxin's Ability to Enhance Response to H1N1 Vaccine," Jan. 12, 2010.
SciClone Press Release, "SciClone and Sigma-Tau Announce Additional Positive Results in Clinical Study Examining Zadaxin's Ability to Enhance Response to H1N1 Vaccine," Feb. 8, 2010.
SciClone Press Release, "SciClone Announces Commencement and Complete Enrollment of Clinical Study Examining Zadaxin's Ability to Enhance the H1N1 Vaccine Led by European Partner," Sigma-Tau, Nov. 30, 2009.
Serrate, S.A. et al., "Modulation of human natural killer cell cytotoxic activity, lymphokine production, and interleukin 2 receptor expression by thymic hormones," The Jounral of Immunology, 139(7):2338-2343 (1987).
Shen, S. Y. et al., "Effect of thymosin alpha-1(Ta1) on heptabax-B(HB) vaccination(V) among hemodialysis (HD) patients(Ps)," Kidney International, 31:217 (1987).

(56) References Cited

OTHER PUBLICATIONS

Sherman, K. E. et al., "Combination therapy with thymosin alpha 1 and interferon for the treatment of chronic hepatitis C infection: a randomized, placebo-controlled double-blind trial," Hepatology, 27(4):1128-1135 (1998).

Scmelev, V. A. et al., "Thymosin Alpha-1 and Hybrid Proteins Consisting of Tumor Necrosis Factor-Alpha and Thymosin Alpha-1 Enchance the Efficacy of Vaccination Against the Causative Agent of Plaque," Zhurnal Mikrobiologii Epidemiologii Immunobiologii, (4):85-89 (1994).

Shrivastava, P. et al., "Effect of Thymosin Alpha 1 on the Antitumor Activity of Tumor-Associated Macrophage-Derived Dendritic Cells," Journal of Biomedical Science, 11:623-630 (2004).

Stein, D. S. et al., "Immune-based therapeutics: Scientific rationale and the promising approaches to the treatment of human immunodeficiency virus-infected individual," Clinical Infectious Diseases, 17(4):749-771 (1993).

Sun, X. et al., "Drug treatment on 680 patients with severe acute respiratory syndrom (SARS): a view of evidence-based medicine," The Cochrane Collaboration [online], [Retrieved on Feb. 8, 2007], <URL: http:/www.cochrane.org/colloquia/abstracts/ottawa/P-141.htm>, 2 pages (2004).

Svedersky, L. P. et al., "Induction and augmentation of mitogen-induced immune interferon production in human peripheral blood lymphocytes by N alpha-desacetylthymosin alpha 1," Eur. J. Immunol., 12(3):244-247 (1982).

Sztein, M. B. et al., "Characterization of the immunoregulatory properties of thymosin alpha 1 on interleukin-2 production and interleukin-2 receptor expression in normal human lymphycytes," International Journal of Immunopharmacology, 11(7):789-800 (1989).

Sztein, M. B. et al., "Modulation of interleukin 2 receptor expression on normal human lymphocytes by thymic hormones," Proc Natl. Acad Sci USA, 83:6107-6111 (1986).

Sztein, M. B. et al., "Thymic hormones—A clinical update," SpringerLink—Springer Seminars in Immunopathology, 9:(1)1-18 (1986).

Tuthill, C., "Issues in pharmaceutical development of thymosin alpha1 from preclinical studies through marketing," Ann. N.Y. Acad. Sci., 1112:351-356 (2007).

Ventola, D. A. et al., "Evaluation of T cell subpopulation and function in thymosin treated spontaneously hypertensive rats," Thymus, 6:129-141 (1984).

Zhang, D-F et al., Suppressor cell function and thymopeptide therapy in viral hepatitis B, Chinese Medical Journal, 99(10):791-798 (1986).

Zhao, Z. et al., "Description and clinical treatment of an early outbreak of severe acute respiratory syndrom (SARS) in Gaungzhou, PR China," Journal of Medical Microbiology, 52:715-720 (2003).

International Search Report and Written Opinion for International Application No. PCT/US2010/034221, mailed Jan. 18, 2011, 10 pages.

International Preliminary Report on Patentability for International Application No. PCT/US2010/034221, mailed Nov. 9, 2011, 6 pages.

* cited by examiner

| CHMP criteria | V<br>N=32 | V+T3.2<br>N=28 | V+T6.4<br>N=32 |
|---|---|---|---|
| Day 21 HI test | | | |
| Percent with SC | 56 | 89 | 88 |
| Percent with HI≥1:40 | 81 | 93 | 94 |
| GMR | 4.15 | 12 | 17 |

* The Day 21 titer of subjects with a second vaccination was carried forward to Day 42 and 84

* The Day 21 titer of subjects with a second vaccination was carried forward to Day 42 and 84

* The Day 21 titer of subjects with a second vaccination was carried forward to Day 42 and 84

* The Day 21 titer of subjects with a second vaccination was carried forward to Day 42 and 84

ALPHA THYMOSIN PEPTIDES AS VACCINE ENHANCERS

PRIORITY

This application claims priority to U.S. Provisional Application No. 61/323,155, filed Apr. 12, 2010, and to U.S. Provisional Application No. 61/176,625, filed May 8, 2009, and to U.S. Provisional Application No. 61/237,932, filed Aug. 28, 2009, each of which is hereby incorporated by reference in its entirety.

FIELD OF THE INVENTION

The present invention relates to the field of vaccines.

BACKGROUND

Humans, livestock and pets often are vaccinated to prevent disease, or reduce the severity of disease. Vaccination results in the production of antibodies, which are serum proteins capable of binding specifically to antigen substances used in the vaccine. This humoral response involves the selection of specific lines of B lymphocytes, and the proliferation and differentiation of the selected cells to yield clones of antibody-producing plasma cells.

Antibody production reaches a peak within several weeks after immunization, and then gradually declines. Because of a constant turnover of serum proteins, the decline in antibody production is accompanied by a corresponding decline in the circulating level of antibodies. However, if the patient is challenged again with the same antigen, a new response curve is initiated more rapidly and more intensely than the first one. This is called a secondary, booster, or anamnestic response, and in healthy patients results in much higher antibody levels with higher affinity to the antigen than the first exposure, or primary immunization. The increased rate of antibody synthesis is the result of an increased number of antibody-producing plasma cells. These cells are scarce in the lymph nodes of the unimmunized patient, which contain mostly small lymphocytes. However, in healthy patients, plasma cells constitute up to 3% of the total lymph node cells after a primary immunization, and as much as 30% of the lymph node cells after a secondary immunization.

The secondary response is said to be due to immunological memory. That is, the healthy organism is able to "remember" its prior exposure to the antigen, and react more promptly and efficiently the second time it is exposed, even if the amount of specific antibodies in the serum has declined to a very low level in the meantime.

Certain conditions such as aging, malnutrition, drug addiction, alcoholism, and certain disease states such as diabetes, chronic renal disease, and AIDS, lead to immunodeficiency (e.g., an immunocompromised subject), in which many immune responses are quenched and vaccination is of reduced effectiveness. Thus, there remains a need in the art for improved vaccines and methods of vaccination, and in particular, for immune deficient patients.

Several administrations of TA1 to patients has shown some promise for enhancing immunity in connection with vaccination. For example, McConnell et al. (*The Gerontologist* 29:188 A (1989)) show that TA1 injections given twice weekly to elderly patients, for a total of eight injections, enhances antibody production in response to influenza vaccination. Shen et al. (*Kidney International* 31:217 (1987)) show that 5 injections of TA1 to hemodialysis patients (previously non-responsive to hepatitis B vaccination), can enhance antibody response to hepatitis B vaccination. However, a more convenient, efficient, and cost effective strategy for enhancing vaccine effectiveness is desirable.

SUMMARY OF THE INVENTION

The present invention provides methods of vaccination as well as pharmaceutical combinations and kits for enhancing vaccine effectiveness, including for the immunodeficient or immunecompromised patients. The invention involves the administration of a vaccine, with one or more doses of thymosin peptide so as to enhance vaccine effectiveness. As disclosed herein, the invention provides higher antibody titers, and/or a more rapid response to vaccination, and/or a longer duration of antibody titers, thereby providing a greater protective effect to the patient, even for individuals who are refractory or low responders to vaccination. For example, in various embodiments, the invention improves the probability of, or speeds the development of, seroconversion and/or seroprotection in response to vaccination, including for refractory or low responders to vaccination. In certain embodiments, the invention provides for vaccine dose sparing, by providing a regimen of thymosin peptide to enhance a patient's response to vaccine antigens.

In one aspect, the invention provides a method for enhancing a subject's response to a vaccine. The method comprises administering a thymosin peptide (e.g., thymosin alpha 1 or "TA1") to the subject at a dose and regimen sufficient to enhance antibody titers and/or sufficient to speed the development of antibody titers, and/or sufficient to extend the duration of antibody titers (e.g., protective antibody titers). In certain embodiments, the subject is human and may be immunodeficient or immunocompromised, such as an elderly patient, diabetic patient, or a patient suffering from chronic renal disease, AIDS, or other immunocompromising illness or condition, including malnutrition, drug abuse, or alcoholism. The subject may be a low responder to vaccination.

In this aspect, the invention may involve vaccination for any condition in which vaccination is an accepted treatment or prevention, such as for any number of infectious diseases. For example, in various embodiments, the infectious disease results from an acute viral infection, such as infection of influenza A (e.g., H1N1 and/or H5N1), influenza B, or SARS, or is a chronic infectious disease such as hepatitis B or hepatitis C, or is an infectious disease resulting in immunodeficiency such as AIDS. Various other types of infectious diseases and other conditions for which vaccination may be enhanced in accordance with the invention are described herein. The vaccination may be a primary vaccination or a secondary vaccination (e.g., a booster).

The vaccination may be against a pandemic illness such as a pandemic flu or a bioterror agent (e.g., anthrax). As disclosed herein, the invention helps speed the development of antibody titers, so as to protect patients sooner, which can be critical for preventing potentially pandemic illness, or for reducing the impact of a bioterror attack or threat.

In accordance with this aspect, the thymosin peptide (e.g., TA1) is administered to the subject at a dose and regimen sufficient to enhance antibody titers and/or sufficient to speed the development of antibody titers, and/or sufficient to extend the duration of (e.g., protective) antibody titers. For example, the thymosin peptide may be administered to a human patient at a dose corresponding to at least about 0.5 mg (e.g., 1.6 mg), or at least about 3 mg (e.g., 3.2 mg), or at least about 5 mg (e.g., 6.4 mg). The thymosin peptide (e.g., TA1) may be administered at a dose within about 2 to about 8 mg, or within about 3 to about 7 mg (e.g., about 3.2 or about 6.4 mg). The thymosin peptide is generally administered from 1 to 4 times, or from 1 to 3 times, and in certain embodiments, is administered once or twice. In these or other embodiments, the TA1 administrations are given to the patient at from about 1 day to about 10 days apart, such as about 5 days to about 9 days apart, e.g., about 7 days apart. For example, the thymosin peptide may be administered prior to vaccination e.g., from 1 to 10 days prior, or from 5 to 9 days prior, and again on the day of vaccination. The thymosin peptide may be administered about 7 days prior to vaccination, and again on the day of vaccination. As disclosed herein, administration of thymosin peptide prior to vaccination and again on the day of vaccination (as shown herein for H1N1 vaccination) leads to a statistically significant increase in the number of immunocompromised patients that achieve seroconversion and/or seroprotection, and speeds the development of antibody titers.

When administered on the same day, the vaccine and the alpha thymosin peptide can be administered separately, or together in a single injection.

Where TA1 is administered prior to and/or concurrently with primary vaccination, a booster vaccination may be administered in certain embodiments. However, in other embodiments, no booster vaccine is necessary. When booster vaccination is desired (for example, where a patient fails to achieve seroconversion or seroprotection after a primary vaccination), one or more doses of thymosin peptide (e.g., 1, 2, 3, or 4) may be administered before the booster (e.g., within about 1 to 10 days prior, including 4, 5, 6, or 7 days prior) including one or more doses of thymosin on the day of booster vaccination.

In another aspect, the invention provides pharmaceutical combinations and kits for convenient vaccine enhancement. The combinations and kits comprise vaccine compositions and thymosin peptides at individual dosage units for practicing the methods of the invention, as described in more detail herein. Generally, the pharmaceutical combination or kit comprises an immune response-triggering vaccine capable of stimulating production in a subject of antibodies to a disease-causing agent. Exemplary vaccine compositions are described herein, and include vaccines against acute and chronic viral, bacterial, or parasitic infections, and in some embodiments is an influenza or hepatitis vaccine. The vaccine composition may comprise a tumor antigen. The vaccine may be selected from a variety of vaccine types, such as killed or inactivated infectious agent(s) (e.g., virus), DNA vaccine, protein subunit vaccine, recombinant vaccine, or toxoid vaccine. The vaccine may comprise a virus vector or may comprise virus-like particles (VLPs). The vaccine may be a live viral vaccine, live attenuated viral vaccine, or inactivated or killed viral vaccine, among others. The vaccine may be adjuvanted or unadjuvanted.

The pharmaceutical combination or kit further comprises a vaccine-enhancing amount of an alpha thymosin peptide (as described in detail herein), which enhances production and/or duration of the antibodies in the subject, in response to the vaccine. The thymosin peptide is generally packaged for independent administration with respect to the vaccine, and may be provided in one, two, three, or four individual dosage units.

In certain embodiments, the combination or kit comprises a first dosage unit comprising an effective amount of thymosin peptide (e.g., TA1), a second dosage unit comprising a vaccine (adjuvanted or unadjuvanted) and an effective amount of the thymosin peptide (in a single or separate dosage unit with respect to the vaccine). In other embodiments, the invention is in the form of a kit comprising one or two vaccine compositions, and one, two, three, or four thymosin dosage units. Such thymosin dosage units may contain thymosin peptide at a dose described herein, for example, between 0.1 and 20 mg, and in some embodiments about or at least 3.2 mg or about 6.4 mg. In each embodiment, the individual dosage units of thymosin peptide may be provided in lyophilized form for reconstitution prior to administration, or may be provided in pre-dosed pens or the like.

In still other aspects, the invention provides a kit for vaccine enhancement, the kit comprising exactly one or two TA1 dosage units, each independently at a dose described herein (e.g., between 0.1 and 20 mg), such as about (or at least) 3.2 or about 6.4 mg. The kit in some embodiments, need not provide the vaccine component. The individual dosage units of thymosin peptide may be provided in lyophilized form for reconstitution prior to administration, or may be provided in aqueous suspension for subcutaneous injection (e.g., via pre-dosed pens or the like). The two dosage units are packaged for sale together, optionally with aqueous diluent for reconstitution of the TA1, for enhancing the effectiveness of a vaccine.

In another aspect, the invention provides a method for reducing a vaccine dose. The method comprises reducing an approved dose of a vaccine, for example, an influenza vaccine or other vaccine, and administering the reduced dose with a regimen of thymosin peptide. The thymosin peptide may be administered at a dose and regimen described herein. In certain embodiments, the vaccine is an influenza virus vaccine, and contains less than 15 μg of any one killed or inactivated influenza virus strain. For example, the vaccine may contain from 2 μg to about 12 μg of killed or inactivated influenza virus from each strain represented.

Other objects and aspects of the invention will be apparent from the following detailed description.

DESCRIPTION OF THE FIGURES

FIG. 6 shows percent seroconversion and antibody titer (geometric mean ratio, or GMR) in patients receiving influenza vaccine alone, or with regimens of 3.2 or 6.4 mg of TA1.

Seroconversion is defined as negative pre-vaccination serum (i.e., HI titer <1:10) and post vaccination HI titer ≥1:40 or a 4-fold increase from non-negative (≥1:10) pre-vaccination HI titer. GMR=ratios of day x/day 0 geometric mean HI titer.

FIG. 7 shows percent seroconversion and geometric mean ratio (HI test) in patients receiving one dose of influenza vaccine, either alone or with regimens of 3.2 or 6.4 mg of TA1.

FIG. 8 shows percent seroconversion and geometric mean ratio (HI test) in patients receiving two doses of influenza vaccine, either alone or with regimens of 3.2 or 6.4 mg of TA1.

FIG. 10 shows percent seroconversion and percent post-vaccination titer <1:40 in patients that were negative at baseline (HI titer <1:10).

DETAILED DESCRIPTION OF THE INVENTION

Figure 1:
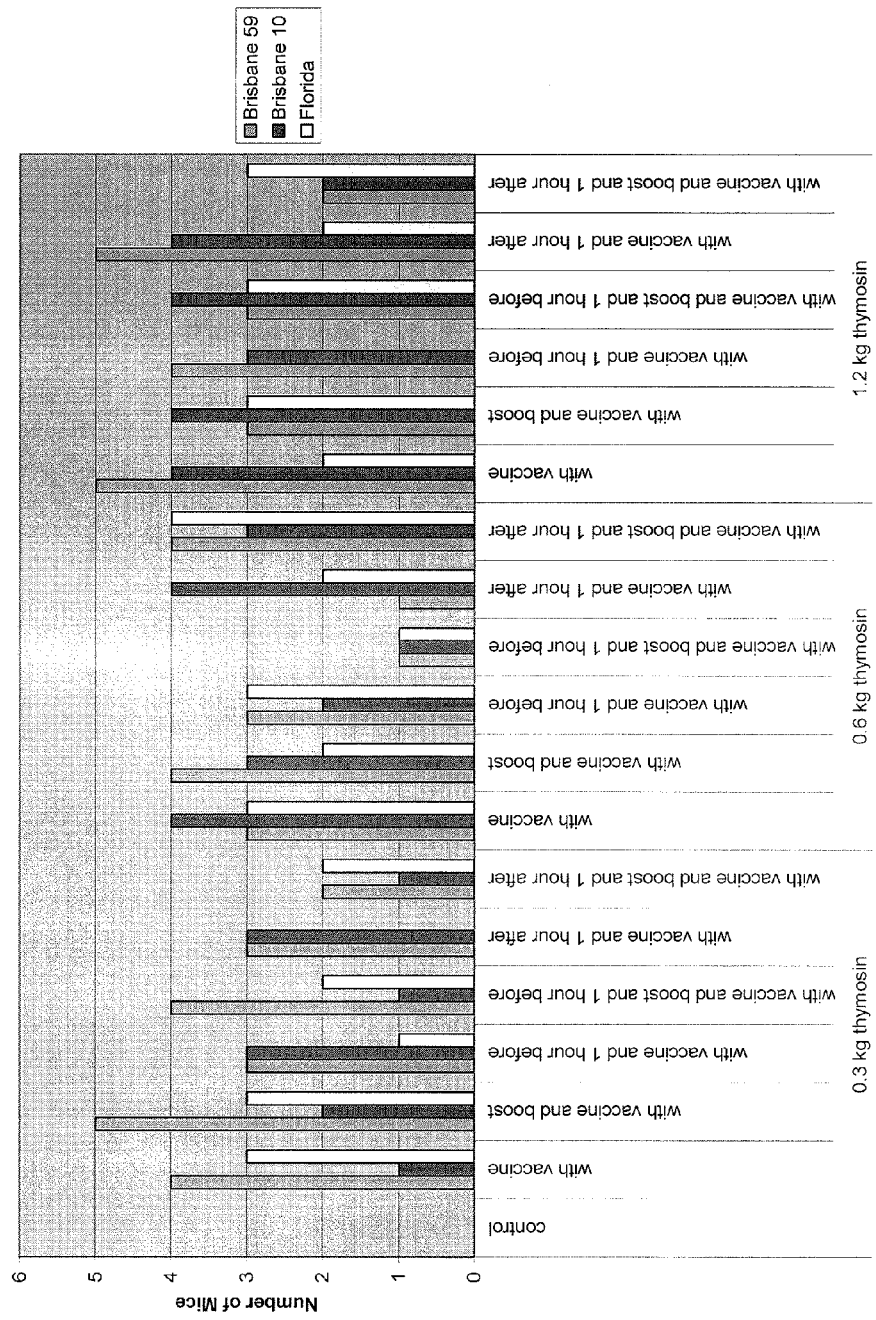
FIG. 1 shows the number of mice reaching the desired antibody titer against 3 strains of influenza, upon receiving thymosin peptide at the indicated dose and at varying times with respect to Fluvirin® administration.

The present invention provides methods for enhancing vaccination as well as pharmaceutical combinations and kits for enhancing vaccine effectiveness, including for the immunodeficient or immunecompromised patient, or patients that are refractory to, or are low responders to, vaccination. As disclosed herein, the invention can provide higher antibody titers and/or speed the development of protective antibody titers, and/or provide for a longer duration of such antibody titers, thereby providing a greater protective effect (or greater probability of a protective effect). For example, in various embodiments, the invention improves the probability of seroconversion and/or seroprotection in response to vaccination.

The invention generally involves administering alpha thymosin peptides ("thymosin peptides") to enhance vaccine effectiveness. Thymosin peptides include thymosin alpha 1 ("TA1"), and peptides having structural homology to TA1. TA1 is a peptide having the amino acid sequence (N-acetyl)-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH (SEQ ID NO: 1). The amino acid sequence of TA1 is disclosed in U.S. Pat. No. 4,079,137, the disclosure of which is hereby incorporated by reference. TA1 is a non-glycosylated 28-amino acid peptide having an acetylated N-terminus, and a molecular weight of about 3108. A synthetic version of TA1 is commercially available in certain countries under the trade name ZADAXIN.

TA1 circulates in serum at about 0.1 to 1.0 ng/ml. Peak plasma levels after injection of 3.2 mg of TA1 (about 40 µg/kg) is approximately 100 ng/ml. The half-life of TA1 in the circulation is about 2 hours.

Thymosin alpha was originally isolated from bovine thymus, where it was shown to reconstitute "immune function" in thymectomized animal models. Thymosin is thought to play a role in inflammatory and innate immune responses, and to facilitate discrimination of self from non-self in mammals. Activation of PAMP (pathogen-associated molecular patterns) ligands by thymosin leads to stimulation of intracellular signal transduction pathways resulting in expression of co-stimulatory molecules, pro-inflammatory cytokines, nitric oxide, and eicosanoids. Thymosin may affect, for example, dendritic cells, T cells, B cells, and NK cells.

Without intending to be bound by theory, it is believed that thymosin peptides (e.g., TA1), among other things, activate Toll-like Receptor 9 (TLR), resulting in increases in Th1 cells, B cells, and NK cells, thereby leading to enhancement of vaccine effectiveness. For example, TA1 may increase or enhance lymphocytic infiltration, secretion of chemotactic cytokines, maturation and differentiation of dendritic cells, secretion of thymopoeitic cytokines including IFN-α, IL-7, and IL-15, and B cell production of antibodies.

The thymosin peptides that find use with the invention include naturally occurring TA1 (e.g., TA1 purified or isolated from tissues), as well as synthetic TA1 and recombinant TA1. In some embodiments, the thymosin peptide comprises the amino acid sequence of SEQ ID NO:1 (where an acylated, e.g., acetylated, N-terminus is optional). In some embodiments, the thymosin peptide comprises an amino acid sequence that is substantially similar to TA1, and maintains the immunomodulatory activity of TA1. The substantially similar sequence may have, for example, from about 1 to about 10 amino acid deletions, insertions, and/or substitutions (collectively) with respect to TA1. For example, the thymosin peptide may have from about 1 to about 5 (e.g., 1, 2, or 3) amino acid insertions, deletions, and/or substitutions (collectively) with respect to TA1.

Thus, the thymosin peptide may comprise an abbreviated TA1 sequence, for example, having deletions of from 1 to about 10 amino acids, or from about 1 to 5 amino acids, or 1, 2 or 3 amino acids with respect to TA1. Such deletions may be at the N- or C-terminus, and/or internal, so long as the immunomodulatory activity of the peptide is substantially maintained. Alternatively, or in addition, the substantially similar sequence may have from about 1 to about 5 amino acid insertions (e.g., 1, 2, or 3 amino acid insertions) with respect to TA1, where the immunomodulatory activity of TA1 is substantially maintained. Alternatively, or in addition, the substantially similar sequence may have from 1 to about 10 amino acid substitutions, where the immunomodulatory activity is substantially maintained. For example, the substantially similar sequence may have from 1 to about 5, or 1, 2, or 3 amino acid substitutions, which may include conservative and non-conservative substitutions. In some embodiments, the substitutions are conservative. Generally, conservative substitutions include substitutions of a chemically similar amino acid (e.g., polar, non-polar, or charged). Substituted amino acids may be selected from the standard 20 amino acids or may be a non-standard amino acid (e.g., a conserved non-standard amino acid).

In some embodiments, the thymosin peptide comprises an amino acid sequence having at least 70% sequence identity to SEQ ID NO:1, while maintaining the immunomodulatory activity of TA1. For example, the thymosin peptide may comprise an amino acid sequence having at least 80%, 90%, or 95% sequence identity to SEQ ID NO:1. The thymosin peptide may comprise an amino acid sequence having 100% sequence identity to SEQ ID NO:1. In all cases, the N-terminus may be optionally acylated (e.g., acetylated) or alkylated, for example, with a C1-10 or C1-C7 acyl or alkyl group.

In certain embodiments, the substantially similar and homologous peptides described above may function at a level of at least about 50%, 70%, 80%, 90%, or about 100% relative to TA1 (SEQ ID NO:1).

The thymosin peptide may be prepared synthetically, for example, by solid phase synthesis, or may be made recombinantly.

The thymosin peptide may be provided in lyophilized form, and reconstituted with sterile (e.g., aqueous) diluent prior to administration. Formulations of thymosin peptide, including formulations for subcutaneous injection, are described elsewhere herein.

In certain embodiments, the thymosin peptide is pegylated to increase its half-life in circulation. Such strategies for increasing the half-life of therapeutic proteins are well known.

In accordance with the invention, the thymosin peptide (e.g., TA1) is administered to the subject at a dose and regimen sufficient to enhance antibody titers and/or sufficient to speed the development of antibody titers, and/or sufficient to extend the duration of (e.g., protective) antibody titers. The invention in various embodiments achieves this goal with relatively few administrations of TA1, thereby rendering the treatment relatively convenient, efficient, and comfortable for the patient, as well as more affordable and effective.

The invention is applicable to both human and veterinary health. Thus, the subject is generally an animal capable of forming antibodies in an immune reaction, and in various embodiments is a mammal, such as a human, livestock (e.g., cow, horse, pig, sheep, etc.), or pet (e.g., cat or dog). In other embodiments, including embodiments in which the vaccine is for an avian influenza, the subject may be a domesticated fowl (e.g., chicken, turkey, duck, or goose).

In certain embodiments, the subject is immunodeficient. An immunodeficient subject may be a subject (e.g., a human subject) exhibiting a reduced capacity to fight infectious disease and/or a reduced capacity to respond to vaccination. Examples of such immunodeficient subjects include an elderly patient, or a patient on hemodialysis (e.g., for treatment of chronic renal disease), AIDS patient, immunodeficiency caused by a genetic defect, malnutrition, drug abuse, alcoholism, or other immunocompromising illness or condition, including cancer.

In certain embodiments, the patient has not been previously vaccinated with the vaccine of interest, and may be negative for specific antibodies against the antigen or pathogen of interest. In other embodiments, the patient was previously vaccinated for a disease or condition, but did not sufficiently respond to the vaccination. For example, the patient in such embodiments did not achieve seroprotection in response to a primary vaccination.

In certain embodiments, the subject is elderly. As animals age, their immune response is reduced, and vaccination effectiveness diminished due to the prevalence of low affinity antibody response. Accordingly, the subject in these embodiments may be a human patient over the age of 45, or over the age of 50. In some embodiments, the subject is a human patient 60 years of age or older, 65 years of age or older, or 70 years of age or older.

In certain embodiments, the subject is being treated with an immune suppressing drug, such as cyclosporine, tacrolimus, rapamycin, or agent that reduces production of antibodies. For example, the subject may be a transplant patient. Transplant patients are generally immunodeficient as a result of administration of anti-rejection drugs such as cyclosporine.

In some embodiments, the patient is on hemodialysis (e.g., due to chronic renal disease). Since hemodialysis requires access to the circulatory system, patients undergoing hemodialysis may expose their circulatory system to microbes, which can lead to sepsis, an infection affecting the heart valves (endocarditis) or an infection affecting the bones (osteomyelitis). Such illnesses and the patient's condition in general may dampen the patient's ability to combat other infectious diseases, including influenza and hepatitis.

In some embodiments, the subject is at risk of infection (e.g., nosocomial infection), while recovering from an invasive surgical procedure, severe injury, severe wound or burn.

In certain embodiments, the subject has a propensity for developing malignancies (e.g., melanoma), which in such patients may be due to a failure of the immune system to recognize such malignancies.

The vaccine may be any vaccine for the treatment or prevention of a condition, and in various embodiments, is a vaccine for an infectious disease. It is believed that the present invention is applicable to a variety of vaccines, and vaccine types, including vaccines comprising killed or inactivated infectious agents (e.g., a virus), DNA vaccines, peptide subunit vaccines, recombinant vaccines, and toxoid vaccines. The vaccine may comprise a virus vector or may comprise virus-like particles (VLPs). The vaccine may be a live viral vaccine, live attenuated viral vaccine, or inactivated or killed viral vaccine.

Examples of suitable vaccines include vaccines against acute or chronic bacterial, viral, or parasitic infections. For example, the vaccine may be against influenza, *Hemophilus influenzae* (e.g., Type B), hepatitis A virus, hepatitis B virus, hepatitis C virus, AIDS virus, tuberculosis, malaria, chlamydia, herpes-zoster virus, cytomegalovirus, pneumococcal pneumonia, meningococcal meningitis, diphtheria, pertussis, tetanus, rabies, *Helicobacter pylori*, lyme disease, polio, and pox virus (e.g., smallpox, cow pox, monkey pox, etc.).

The vaccine in some embodiments is multivalent. For example, the vaccine may be a seasonal trivalent influenza vaccine, or may comprise antigenic components from 2 or 3 bacterial and/or viral infectious agents.

Further exemplary vaccines include inactivated polio vaccine, yellow fever vaccine, Japanese encephalitis vaccine, adenovirus vaccine, human papilloma virus vaccine, pneumococcal polysaccharide vaccine, anthrax vaccine, typhoid vaccine, plague vaccine, cholera vaccine, tuberculosis vaccine (or *Bacillus* Calmette-Guérin vaccine), and meningococcal vaccine.

Exemplary commercially available vaccines for which the invention may be effective for enhancing an immune response include: influenza vaccines such as those available under the trade names FLUARIX, FLUVIRIN, FOCETRIA, FLUZONE, FLULAVAL, AFLURIA, FLUMIST, and comparable vaccines containing the same or similar antigenic components; and hepatitis vaccines such as those available under the trade names HAVRIX, VAQTA, ENERIX-B, RECOMBIVAX HB, COMVAX, PEDIARIX, and TWINRIX, as well as comparable vaccines containing the same or similar antigenic components In accordance with certain embodiments, the present invention is applicable to vaccines against a respiratory virus, such as SARS, RSV, or influenza virus, e.g., influenza type A, type B and/or type C, and including potentially pandemic influenza virus infections, including swine flu infections and/or avian flu infections. For example, the invention is applicable to vaccines against H1N1 infection and/or H5N1 infection in a subject.

Influenza spreads around the world in seasonal epidemics, resulting in the deaths of hundreds of thousands annually, sometimes millions in a pandemic year. Vaccinations against influenza are usually given to people in developed countries and to farmed poultry. The most common human vaccine is the trivalent influenza vaccine (TIV) that contains purified and inactivated material from three viral strains. Typically, this vaccine includes material from two Influenza A virus subtypes and one Influenza B virus strain. The TIV carries no risk of transmitting the disease, and it has very low reactivity.

In accordance with certain embodiments, the invention is applicable to vaccines against influenza A swine flu and/or influenza A avian flu. Swine flu vaccines to which the invention is applicable include, without limitations, vaccines against types H1N1, H1N2, H3N1, H3N2 and/or H2N3. Avian flu vaccines to which the invention is applicable include, without limitation, vaccines against types H1N1, H1N8, H2N9, H3N8, H3N2, H4N6, H4N3, H5N3, H5N9, H5N1, H6N2, H6N8, H6N5, H6N1, H7N7, H7N1, H7N3, H8N4, H9N2, H9N6, H10N7, H10N8, H11N6, H11N9, H12N5, H13N6, H13N4 and/or H15N9. In certain embodiments, the avian flu vaccine is against H5N1, H7N3, H7N7 and/or H9N2. Exemplary avian influenza strains include:

TABLE 1

Avian Influenza Strains

| HA subtype designation | NA subtype designation | Avian influenza A viruses |
|---|---|---|
| H1 | N1 | A/duck/Alberta/35/76(H1N1) |
| H1 | N8 | A/duck/Alberta/97/77(H1N8) |
| H2 | N9 | A/duck/Germany/1/72(H2N9) |
| H3 | N8 | A/duck/Ukraine/63(H3N8) |
| H3 | N8 | A/duck/England/62(H3N8) |
| H3 | N2 | A/turkey/England/69(H3N2) |
| H4 | N6 | A/duck/Czechoslovakia/56(H4N6) |
| H4 | N3 | A/duck/Alberta/300/77(H4N3) |
| H5 | N3 | A/tern/South Africa/300/77(H4N3) |
| H5 | N9 | A/turkey/Ontario/7732/66(H5N9) |
| H5 | N1 | A/chick/Scotland/59(H5N1) |
| H6 | N2 | A/turkey/Massachusetts/3740/65(H6N2) |
| H6 | N8 | A/turkey/Canada/63(H6N8) |
| H6 | N5 | A/shearwater/Australia/72(H6N5) |
| H6 | N1 | A/duck/Germany/1868/68(H6N1) |

TABLE 1-continued

Avian Influenza Strains

| HA subtype designation | NA subtype designation | Avian influenza A viruses |
|---|---|---|
| H7 | N7 | A/fowl plague virus/Dutch/27(H7N7) |
| H7 | N1 | A/chick/Brescia/1902(H7N1) |
| H7 | N3 | A/turkey/England/639H7N3) |
| H7 | N1 | A/fowl plague virus/Rostock/34(H7N1) |
| H8 | N4 | A/turkey/Ontario/6118/68(H8N4) |
| H9 | N2 | A/turkey/Wisconsin/1/66(H9N2) |
| H9 | N6 | A/duck/Hong Kong/147/77(H9N6) |
| H10 | N7 | A/chick/Germany/N/49(H10N7) |
| H10 | N8 | A/quail/Italy/1117/65(H10N8) |
| H11 | N6 | A/duck/England/56(H11N6) |
| H11 | N9 | A/duck/Memphis/546/74(H11N9) |
| H12 | N5 | A/duck/Alberta/60/76/(H12N5) |
| H13 | N6 | A/gull/Maryland/704/77(H13N6) |
| H14 | N4 | A/duck/Gurjev/263/83(H14N4) |
| H15 | N9 | A/shearwater/Australia/2576/83(H15N9) |

In accordance with a further embodiment, the invention is applicable to vaccines against Influenza C swine flu in a subject.

In other embodiments, the vaccine is for the treatment or prevention of a cancer, and the vaccine comprises one or more tumor antigens, or may involve autologous cellular immunotherapy. The cancer vaccine may involve an immunotherapy the same or similar to that available under the trade name PROVENGE, or a similar or comparable treatment.

The vaccine to be enhanced in accordance with the invention may be a primary or secondary vaccination (e.g., a booster).

Generally, the vaccine composition is administered to the subject in an amount determined as effective in each embodiment, or at (or below) an amount for which the selected vaccine is approved for use in patients by a government regulatory agency (e.g. in the absence of thymosin peptide administration). The immune-response triggering amount will depend on the composition of the vaccine. Generally, the antigenic composition of the vaccine may be administered to the subject within the range of from about $1 \times 10^{-9}$ g to about $1 \times 10^{-3}$ g, and more typically within the range from about $1 \times 10^{-8}$ g to about $1 \times 10^{-4}$ g. The vaccine may be administered by intramuscular or subcutaneous injection, or by intranasal administration, or other route shown to be effective for the particular vaccine of interest.

In some embodiments, the invention provides for a reduced vaccine dose, including methods for reducing a vaccine dose. The method comprises administering thymosin peptide at a regimen described herein, with a dose of vaccine less than the dose approved by a regulatory agency for the vaccine alone. In these embodiments, the invention enables vaccine sparing, which can be critical for vaccinating a population against a pandemic illness or bioterror threat. In certain embodiments, the vaccine is an influenza vaccine, and the vaccine contains less than 15 μg of any one killed or inactivated influenza virus strain. For example, the vaccine (e.g., FLUARIX or comparable vaccine) may contain from 2 μg to about 12 μg of killed or inactivated influenza virus from each strain represented.

The thymosin peptide is administered to the subject at a dose sufficient to enhance antibody titers, and/or sufficient to speed the development of antibody titers, and/or sufficient to extend the duration of protective antibody titers. For example, in various embodiments the thymosin peptide is administered to a human patient at a dose corresponding to at least about 0.5 mg (e.g., at least about 1.6 mg), at least about 3 mg (e.g., at least about 3.2 mg), or at least about 5 mg (e.g., at least about 6.4 mg) of TA1. The thymosin peptide may generally be administered within the range corresponding to about 0.1 to 20 mg of TA1, or about 1 to 10 mg of TA1, or about 2 to 10 mg of TA1, or about 2 to 8 mg of TA1, or about 2 to 7 mg of TA1. In certain embodiments, the dosage unit is within a range of 3 to 6.5 mg, such as about 3.2 or 6.4 mg of TA1. Doses may be adjusted for the species of the subject or patient, but in each case, approximately correspond to the human equivalent of TA1 (mg/kg).

The thymosin peptide (e.g., TA1) may be administered by any effective route, including by subcutaneous injection, intramuscular injection, intravenous injection or infusion, and orally. In certain embodiments, the thymosin peptide is administered by subcutaneous injection. Generally, the scheduled dose of thymosin may be administered as a single dose (e.g., injection), or may be spaced out over the course of 24 hours or less, for example, by continuous infusion or repeated injection, or the like. The scheduled dose of thymosin peptide may be administered as a single injection.

In some embodiments, such as for immobilized or hospitalized patients, the TA1 may be administered by continuous infusion. Continuous infusion of TA1 is described in detail in US 2005/0049191, the entire disclosure of which is hereby incorporated by reference. Briefly, continuous infusion of thymosin peptide maintains an immune stimulating-effective amount of a thymosin peptide in a patient's circulatory system for a longer period. The plasma half-life of subcutaneously injected TA1 is about two hours, and thus, according to certain embodiments, the thymosin peptide may be administered to the patient for treatment periods of at least about 6, 10, 12 hours, or longer, which may improve effectiveness in some embodiments. The infusion may be carried out by any suitable means, such as by minipump.

Alternatively, the thymosin peptide can be administered by a plurality of injections (sub-doses of thymosin peptide) on a treatment day, so as to substantially continuously maintain an immune stimulating-effective amount of the thymosin peptide in the patient's circulatory system for a longer period of time. Suitable injection regimens may include an injection every 2, 3, 4, 6, etc. hours on the day of administration (e.g., from 2 to 5 injections), so as to substantially continuously maintain the immune stimulating-effective amount of the thymosin peptide in the patient's circulatory system on the day of thymosin treatment.

The immune stimulating-effective amounts of a thymosin peptide (e.g. TA1) may be substantially continuously maintained in a patient's circulatory system by administering the TA1 peptide to the patient at a rate within a range of about 0.0001-0.1 mg/hr/Kg patient body weight. Exemplary administration rates are within a range of about 0.0003-0.03 mg/hr/Kg patient body weight. For continuous infusion, the TA1 peptide is present in a pharmaceutically acceptable liquid carrier, such as water for injection, or saline in physiological concentrations.

The thymosin peptide is generally administered from 1 to 4 times, or from 1 to 3 times, and in certain embodiments, is administered twice (e.g., on two treatment days). For example, the alpha thymosin peptide is administered prior to, along with and/or after a primary or secondary vaccination. Where the thymosin peptide is administered to enhance primary vaccination as disclosed herein, a booster vaccination may optionally follow at a later time. In certain embodiments, the vaccine is administered as a first, primary dose of vaccine, and the alpha thymosin peptide is administered at least one of prior to, concurrently with or after the primary dose. In certain embodiments, the alpha thymosin peptide is administered after the primary dose of vaccine, and prior to a booster dose of said vaccine. Thus, the thymosin peptide may be administered prior to and along with primary and/or secondary vaccination.

The timing of thymosin administration is selected to enhance antibody titers (e.g., the development or level of antibody titers) and/or duration of (e.g., protective) antibody titers. For example, in certain embodiments, the thymosin peptide administrations are given about 5 days to about 9 days apart, and in various embodiments are administered about 6, 7, or 8 days apart. The thymosin administrations may be given about 7 days apart. In other embodiments, the thymosin peptide administrations are given 1, 2, 3, or 4 days apart.

In some embodiments, the thymosin peptide is administered prior to primary vaccination, and again on the day of primary vaccination. For example, thymosin peptide may be administered from 1 to 10 days prior to primary vaccination, such as from about 5 to about 9 days prior to primary vaccination, and again on the day of primary vaccination. The thymosin peptide may be administered about 7 days prior to primary vaccination, and again on the day of primary vaccination. Administration of thymosin peptide prior to vaccination and again on the day of vaccination leads to a statistically significant increase in the number of immunocompromised patients achieving protective antibody titers. For example, patients receiving TA1 in accordance with the invention may achieve seroconversion for at least 21 days, at least 42 days, at least 84 days, or longer.

In other embodiments, the vaccination method comprises administering to an immunodeficient animal a first dose of an immune response-triggering vaccine capable of stimulating production in an animal of antibodies to a disease-causing agent foreign to the animal (as described above); then, within a time period of between about 1 week and about 2 months after administration of said first dose, administering to the animal either: 1) a vaccine effectiveness-enhancing amount of an alpha thymosin peptide which enhances production of the antibodies in the animal in response to the vaccine; or 2) a booster dose of the vaccine, along with a vaccine effectiveness-enhancing amount of the alpha thymosin peptide, so as to enhance effectiveness of the vaccine in said animal.

In certain embodiments, the alpha thymosin peptide permits smaller doses of vaccine to be administered while maintaining vaccine effectiveness in triggering an immune response. The invention thus provides vaccine dose sparing, which may be critical for pandemic illness such as pandemic influenza outbreak, or for protecting a population from a threat or attack of bioterrorism.

The alpha thymosin peptide may be administered in connection with a secondary (booster) vaccination dose. The secondary or booster vaccination is generally administered within a time period of about 1 week to about 2 months after administration of the first (primary) vaccine dose. In certain embodiments, the booster vaccine is administered within about 10 to 45 days of the first vaccine dose, or within about 10 to 30 days of administration of the first vaccine dose, and according to some embodiments, within about 10 to 20 days of administration of the first vaccine dose. However, while booster vaccinations may be administered in certain embodiments, in other embodiments, no booster vaccine is administered.

In accordance with one embodiment, one or more doses of thymosin peptide is administered to the recipient several days prior (e.g., 1 to 10 days prior) to administration of a secondary (booster) vaccine dose, e.g., about 2 to 9 days (e.g., about 5 to 7 days), or in some embodiments 3 to 4 days prior to administration of the secondary (booster) vaccine dose. In certain embodiments, an alpha thymosin peptide also is administered concurrently with administration of the secondary (booster) vaccine dose.

When administered on the same day, the vaccine and the alpha thymosin peptide can be administered separately, or together in a single injection. When a vaccine and the alpha thymosin peptide are administered concurrently, they can be provided as a single composition including the vaccine and the alpha thymosin peptide.

In another aspect, the invention provides pharmaceutical combinations and kits for vaccination, or for enhancing vaccination. The combinations and kits comprise vaccine compositions and thymosin peptides at individual dosage units for practicing the methods of the invention, as described above, and with reference to the following description.

The pharmaceutical combination or kit may comprise an immune response-triggering vaccine capable of stimulating production of antibodies in a subject, as described in detail above, together with individual dosage units of thymosin peptide (as described above). In particular embodiments, the invention provides a kit for enhancing influenza vaccination, the kit comprising one or two dosage units of an influenza vaccine, such as, for example, an influenza vaccine available under the trade name FLUARIX, FLUVIRIN, FOCETRIA, FLUZONE, FLULAVAL, AFLURIA, or FLUMIST, or a comparable vaccine containing the same or similar antigenic components. In other embodiments, the invention provides a kit for enhancing hepatitis vaccination, and thus comprises one or two dosage units of a hepatitis vaccine, such as a hepatitis vaccine selected from those available under the trade names HAVRIX, VAQTA, ENERIX-B, RECOMBIVAX HB, COMVAX, PEDIARIX, and TWINRIX, as well as comparable vaccines containing the same or similar antigenic components.

In addition to a vaccine composition, the pharmaceutical combination or kit further comprises a vaccine effectiveness-enhancing amount of an alpha thymosin peptide, as described in detail above. The alpha thymosin peptide (e.g., TA1) may be provided in individual dosage units, such as 1, 2, 3 or 4 dosage units. Such dosage units may be provided in lyophilized form for reconstitution prior to administration with sterile diluent (which may also be provided as a component of the kit), or otherwise formulated as a liquid suspension for injection as described herein, such as for subcutaneous injection. For example, the thymosin peptide may be provided in pre-dosed pens and the like. In various embodiments, the thymosin peptide dosage unit corresponds to at least about 0.5 mg of TA1, at least about 3 mg, at least about 5 mg, or generally within the range corresponding to about 0.1 to 20 mg of TA1, or about 1 to 10 mg of TA1, or about 2 to 10 mg of TA1, or about 2 to 8 mg of TA1, or about 2 to 7 mg of TA1. In certain embodiments, the dosage unit is within a range of 3 to 6.5 mg, such as about 3.2 or 6.4 mg of TA1.

In certain embodiments, the combination or kit comprises a first dosage unit comprising an effective amount of thymosin peptide at a dose as described herein (e.g., from 1 to 10 mg, or about 3.2 or about 6.4 mg of TA1), a second dosage unit comprising a vaccine (e.g., a seasonal influenza vaccine or H1N1 or H5N1 vaccine, or a hepatitis vaccine as described), and a third dosage unit comprising an effective amount of the thymosin peptide at a dose described herein (e.g., from 1 to 10 mg, or about 3.2 or about 6.4 mg of TA1). The kit may further comprise a sealed container of sterile diluent (e.g., a sterile aqueous diluent) for reconstituting TA1 provided in lyophilized form. The components may be packaged for sale together.

Compositions including a vaccine and/or the thymosin peptide can also include one or more pharmaceutically acceptable carriers and optionally other therapeutic ingredients. Formulations suitable for injection or infusion include aqueous and non-aqueous sterile injection solutions which may optionally contain antioxidants, buffers, bacteriostats and solutes which render the formulations isotonic with the blood of the intended recipient, and aqueous and non-aqueous sterile suspensions which may include suspending agents and thickening agents. For example, the thymosin peptide (e.g., TA1) may be provided as a lyophilized formulation with mannitol and sodium phosphate. The formulations may be presented in unit-dose or multi-dose containers, for example, sealed ampules and vials, and may be stored in a freeze-dried (lyophilized) condition requiring only the addition of the sterile liquid carrier, for example, water for injection, immediately prior to use. In certain embodiments, the kit of the invention provides two individual ampules or vials of lyophilized TA1, each containing a dose of lyophilized TA1 as described (e.g., from 1 to 10 mg, or about 3.2 or about 6.4 mg), and packaged together for sale, with sealed vial or other container containing sterile aqueous diluent.

In one exemplary embodiment, the invention is in the form of a kit packaged for sale, comprising an individual dosage unit of an influenza vaccine (e.g., seasonal trivalent vaccine or H1N1, or H5N1 vaccine), and exactly one or two doses of TA1, each at 5 mg or more (e.g., about 6.4 mg), and which are in a lyophilized form to be reconstituted with liquid carrier for subcutaneous administration. Sterile liquid carrier (e.g., sterile water) in individual units may also be provided for convenient reconstitution of the TA1 dosage units.

In still other aspects, the invention provides a kit for vaccine enhancement, the kit comprising exactly two thymosin peptide dosage units, each at a dose as described herein, for example, between 1 and 10 mg, or about 3.2 or 6.4 mg. The individual dosage units of thymosin peptide may be provided in lyophilized form for reconstitution prior to administration, or may be provided in pre-dosed pens or the like. When provided in lyophilized form, one or two vials of sterile aqueous carrier (e.g., from about 0.5 to about 3 mls, e.g., about 1 ml) for reconstitution of the TA1 are also provided. The two dosage units, and carrier if provided, are packaged for sale together, for enhancing the effectiveness of a vaccine. The vaccine need not be provided in this aspect.

EXAMPLES

Example 1

Enhancement of H1N1 Vaccination in Mice

Summary

A study was conducted to determine the potential of TA1 (thymalfasin) to enhance the formation of anti-influenza antibodies in CD-1 mice following different vaccination schedules with the seasonal influenza vaccine Fluvirin® 2008-2009. The mice received either control article or vaccine on Study Days (SDs) 1 and 10 or SDs 8 and 17. The mice also received different doses of TA1 at different times in relation to the vaccine administration. Both the control article and vaccine were administered via intramuscular injection to both the right and left hind limbs; TA1 was administered by the intraperitoneal route. All mice were given a fixed dose of control/vaccine regardless of the body weight. The mice were observed twice daily for mortality, moribundity, general health, and signs of toxicity; body weights were recorded prior to dosing. Blood samples were collected on either SD 20 or 27 (ten days after final vaccine administration) and these samples were analyzed for HAI antibody production. Following the blood collection, all animals were euthanized and discarded without necropsy.

The results indicate that the HAI titer was greater in mice receiving both TA1 and FLUVIRIN vs. those receiving FLUVIRIN alone. In addition, the highest dose of TA1 used in this study (1.2 mg/kg) increased the titers more consistently when compared to the other doses. Furthermore, the best dosing schedule was administration of TA1 seven days prior to and on the day of FLUVIRIN vaccination on SD 8, as all animals achieved desired anti-influenza antibodies in all tester strains.

Experimental Study

Thymosin alpha 1 (TA1; trade name ZADAXIN®) is approved and commercially available. TA1 is found naturally in the circulation and produced in the body's thymus gland. ZADAXIN® (a synthetic version of thymosin alpha 1) stimulates the immune system at least in part by affecting T cells and NK cells.

TA1 has an excellent safety record. In clinical studies to date, more than 3,000 patients, including adults, the elderly, and children, with viral hepatitis B and hepatitis C, primary immunodeficiency diseases, and numerous cancers have been treated with TA1 with virtually no drug-related side effects. Nor has there been any worsening of side effects when TA1 is combined with other agents such as interferon and chemotherapy. In animal studies, TA1 has been administered in doses as high as 800 times the recommended human dose with no evidence of adverse clinical signs.

Clinical trials have demonstrated that TA1 increases the response to influenza and hepatitis B vaccines in the elderly and hemodialysis patients; however, the treatment regimen has involved 8 injections of TA1 subsequent to vaccination. The current study was conducted to determine the potential of different doses and dosing regimens (primarily with fewer injections) of TA1 to enhance the formation of anti-influenza antibodies in CD-1 mice following two different vaccination schedules with the seasonal influenza vaccine Fluvirin® 2008-2009.

Appropriate numbers of male CD-1 mice were purchased from Charles River Laboratories. The animals weighed 25 to 40 grams and were 7 to 9 weeks of age at the first dose. All animals received Certified Global Harlan Teklad Laboratory Diet 2018 (pellets) and water via an automatic watering system and/or water bottles. Animals were individually housed in polycarbonate cages with Certified SaniChip® hardwood bedding and suspended on stainless steel racks. The temperature and humidity ranges were 18 to 26° C. and 30 to 70%, respectively.

The control article was 0.9% Sodium Chloride for Injection, USP, and was stored at room temperature.

TA1 was diluted with phosphate buffered saline to the appropriate concentrations and stored at 2 to 8° C. until used.

Fluvirin® 2008-2009 was diluted with 0.9% Sodium Chloride for Injection, USP, to the appropriate concentration and used on day of formulation.

The study was divided into 2 cohorts, depending upon the vaccine dosing schedule; five mice/group were randomly assigned to each group. The first cohort of mice (20 groups) received control article or vaccine on Study Days (SD) 8 (Vaccine) and 17 (Boost) and the second cohort of mice (23 groups) received control article or vaccine on SDs 1 (Vaccine) and 10 (Boost). TA1 administration occurred as indicated in Tables 3 and 4.

The control article (0.9% Sodium Chloride for Injection, USP) and vaccine (9 µg/dose Fluvirin® 2008-2009) were both administered via intramuscular injection to both the right and left hind limbs at a fixed dose of 0.05 mL of control article/vaccine (regardless of the body weight).

TA1 (0.3, 0.6 or 1.2 mg/kg/dose) was administered by the intraperitoneal route at a dose volume of 1 mL/kg.

TABLE 2

| Mouse/Ferret/Human Dosing Schedule | | | |
|---|---|---|---|
| Human Dose | | Mouse Dose | Ferret Dose |
| mg/person | mg/kg | mg/kg | mg/kg |
| 1.6 | 0.02 | 0.3 | 0.14 |
| 3.2 | 0.04 | 0.6 | 0.28 |
| 6.4 | 0.08 | 1.2 | 0.57 |

Animals were observed twice daily for mortality, moribundity, general health, and signs of toxicity. Animals were observed for skin and fur characteristics, injection sites, eye and mucous membranes, respiratory, circulatory, and autonomic and central nervous systems, somatomotor and behavior patterns. Body weights were recorded prior to dosing only.

Blood samples for analysis of influenza antibody titer (HAI analysis) were collected from all the animals via cardiac stick on SD 20 or SD 27 (ten days after final control article/vaccine administration). Following the blood collection, all animals were euthanized by $CO_2$ inhalation, exsanguinated and disposed of without necropsy.

HAI analysis was performed in triplicate against the 3 vaccine strains present in the Fluvirin® 2008-2009 vaccine (Florida [B], Brisbane 10 and Brisbane).

TABLE 3

| Cohort 1 (Control Article/Vaccine Administered on SD 1 and 10) | | | |
|---|---|---|---|
| Group | Treatment | Time of TA 1 Administration | TA 1 Dose Level (mg/kg/dose) |
| 1 | Control Article | Not applicable - Control article (saline) will be administered on SD 1 and 10 | 0 |
| 2 | Vaccine only | Not applicable - Vaccine will be administered on SD 1 and 10 | 0 |
| 3 | Vaccine/TA 1 | TA 1 will be administered at the same time as the vaccine on SD 1 but will not be administered on SD 10 | 0.3 |
| 4 | Vaccine/TA 1 | TA 1 will be administered at the same time as the vaccine on SD 1 and 10 | |

TABLE 3-continued

Cohort 1 (Control Article/Vaccine Administered on SD 1 and 10)

| Group | Treatment | Time of TA 1 Administration | TA 1 Dose Level (mg/kg/dose) |
|---|---|---|---|
| 5 | Vaccine/TA 1 | 1 hr before vaccine administration on SD 1 and at the time of vaccine administration on SD 1 but not on SD 10 | |
| 6 | Vaccine/TA 1 | 1 hr before vaccine administration on SD 1 and 10 and at the time of vaccine administration on SD 1 and SD 10 | |
| 7 | Vaccine/TA 1 | At the time of vaccine administration on SD 1 and 1 hr after administration on SD 1 but not on SD 10 | |
| 8 | Vaccine/TA 1 | At the time of vaccine administration on SD 1 and 10 and one hour after vaccine administration on SD 1 and 10 | |
| 9 | Vaccine/TA 1 | TA 1 will be administered at the same time as the vaccine on SD 1 but will not be administered on SD 10 | 0.6 |
| 10 | Vaccine/TA 1 | TA 1 will be administered at the same time as the vaccine on SD 1 and 10 | |
| 11 | Vaccine/TA 1 | 1 hr before vaccine administration on SD 1 and at the time of vaccine administration on SD 1 but not on SD 10 | 0.6 |
| 12 | Vaccine/TA 1 | 1 hr before vaccine administration on SD 1 and 10 and at the time of vaccine administration on SD 1 and SD 10 | |
| 13 | Vaccine/TA 1 | At the time of vaccine administration on SD 1 and 1 hr after administration on SD 1 but not on SD 10 | |
| 14 | Vaccine/TA 1 | At the time of vaccine administration on SD 1 and 10 and one hour after vaccine administration on SD 1 and 10 | |
| 15 | Vaccine/TA 1 | TA 1 will be administered at the same time as the vaccine on SD 1 but will not be administered on SD 10 | 1.2 |
| 16 | Vaccine/TA 1 | TA 1 will be administered at the same time as the vaccine on SD 1 and 10 | |
| 17 | Vaccine/TA 1 | 1 hr before vaccine administration on SD 1 and at the time of vaccine administration on SD 1 but not on SD 10 | |
| 18 | Vaccine/TA 1 | 1 hr before vaccine administration on SD 1 and 10 and at the time of vaccine administration on SD 1 and SD 10 | |
| 19 | Vaccine/TA 1 | At the time of vaccine administration on SD 1 and 1 hr after administration on SD 1 but not on SD 10 | |
| 20 | Vaccine/TA 1 | At the time of vaccine administration on SD 1 and 10 and one hour after vaccine administration on SD 1 and 10 | |

TABLE 4

Cohort 2 (Control Article/Vaccine Administered on SD 8 and 17)

| Group | Treatment | Time of TA 1 Administration | TA 1 Dose Level (mg/kg/dose) |
|---|---|---|---|
| 1 | Control Article | Not applicable - Control article (saline) will be administered on SD 8 and 17 | 0 |
| 2 | Vaccine only | Not applicable - Vaccine will be administered on SD 8 and 17 | 0 |
| 3 | Vaccine/TA 1 | TA 1 will be administered at the same time as the vaccine on SD 8 | 0.3 |
| 4 | Vaccine/TA 1 | 1 hr before and at the same time as vaccine administration on SD 8 | |
| 5 | Vaccine/TA 1 | 1 hr after and at the same time as vaccine administration on SD 8 | |
| 6 | Vaccine/TA 1 | SD 7 - the day prior to and at the same time as vaccine administration on SD 8 | |
| 7 | Vaccine/TA 1 | SD 9 - the day after and at the same time as vaccine administration on SD 8 | |

TABLE 4-continued

Cohort 2 (Control Article/Vaccine Administered on SD 8 and 17)

| Group | Treatment | Time of TA 1 Administration | TA 1 Dose Level (mg/kg/dose) |
|---|---|---|---|
| 8 | Vaccine/TA 1 | SD 1 - 7 days prior to and at the same time as vaccine administration on SD 8 | |
| 9 | Vaccine/TA 1 | At the same time as vaccine administration on SD 8 and 17 | |
| 10 | Vaccine/TA 1 | TA 1 will be administered at the same time as the vaccine on SD 8 | 0.6 |
| 11 | Vaccine/TA 1 | 1 hr before and at the same time as vaccine administration on SD 8 | |
| 12 | Vaccine/TA 1 | 1 hr after and at the same time as vaccine administration on SD 8 | |
| 13 | Vaccine/TA 1 | SD 7 - the day prior to and at the same time as vaccine administration on SD 8 | 0.6 |
| 14 | Vaccine/TA 1 | SD 9 - the day after and at the same time as vaccine administration on SD 8 | |
| 15 | Vaccine/TA 1 | SD 1 - 7 days prior to and at the same time as vaccine administration on SD 8 | |
| 16 | Vaccine/TA 1 | At the same time as vaccine administration on SD 8 and 17 | |
| 17 | Vaccine/TA 1 | TA 1 will be administered at the same time as the vaccine on SD 8 | 1.2 |
| 18 | Vaccine/TA 1 | 1 hr before and at the same time as vaccine administration on SD 8 | |
| 19 | Vaccine/TA 1 | 1 hr after and at the same time as vaccine administration on SD 8 | |
| 20 | Vaccine/TA 1 | SD 7 - the day prior to and at the same time as vaccine administration on SD 8 | |
| 21 | Vaccine/TA 1 | SD 9 - the day after and at the same time as vaccine administration on SD 8 | |
| 22 | Vaccine/TA 1 | SD 1 - 7 days prior to and at the same time as vaccine administration on SD 8 | |
| 23 | Vaccine/TA 1 | At the same time as vaccine administration on SD 8 and 17 | |

Results

All animals survived until scheduled termination and there were no test article-related clinical/cageside observations or body weight effects noted in any animal.

When two doses of TA1 were administered to male CD-1 mice at different schedules in relationship to vaccination with Fluvirin® 2008-2009, the HAI titer was generally greater in animals receiving both TA1 and Fluvirin® 2008-2009 vs those receiving Fluvirin® 2008-2009 alone.

Figure 2:
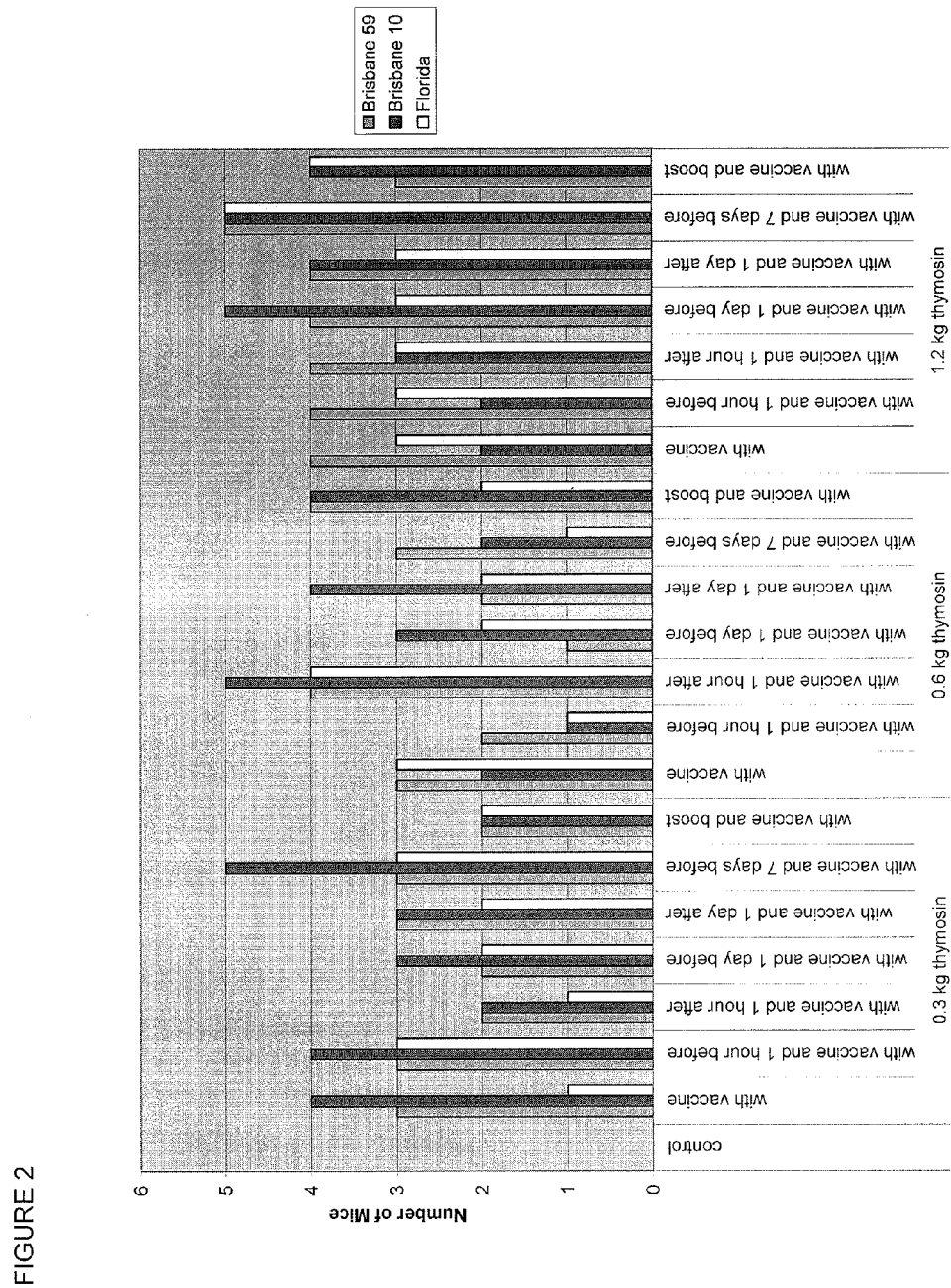
FIG. 2 shows the number of mice reaching the desired antibody titer upon receiving thymosin peptide at the indicated dose and at varying times with respect to vaccine administration (Fluvirin®). As shown, mice receiving thymosin peptide with the vaccine, and seven days prior to the vaccine, were all protected against three strains of influenza.

Under the different schedules investigated in the current study, the 1.2 mg/kg dose of TA1 increased the titers more consistently when compared to the other doses. See FIGS. 1 and 2. A dose of 1.2 mg/kg in mice is equivalent to a dose of approximately 6.4 mg in humans.

Furthermore, the best dosing schedule was TA1 administration seven days prior to and on day of Fluvirin® 2008-2009 vaccination on SD 8, as all animals achieved desired anti-influenza antibodies in all tester strains with this regimen. See FIGS. 1 and 2.

Thus, as determined by HAI titer assay, TA1 enhances the formation of anti-influenza antibodies in CD-1 mice vaccinated with two 9 µg doses of Fluvirin® 2008-2009. The most effective dosing regimen was 1.2 mg/kg TA1 given twice: seven days prior to and on the day of vaccination.

Example 2

Enhancement of H1N1 Vaccination in Ferrets

Thymosin has been shown to exert immunomodulation in several microbial and tumor settings by a variety of mechanisms which include potentiation of antibody responses. In the efforts to control the ongoing influenza pandemia caused by the new A/H1N1 virus of swine origin, a voluntary, mass vaccination will be implemented in most countries, and vaccines with or without adjuvants will be used. At least some of these vaccines will require a post-1 month booster dose to induce appreciable production of virus-neutralizing antibodies in most vaccinees. Moreover, the availability of these vaccines for the whole target population is doubtful. It is therefore important to assess whether suitable doses of thymosin, administered separately but concomitantly with the influenza vaccine may potentiate the antibody responses to the virus.

Experimental Study

Influenza-free ferrets are very responsive to influenza virus, and thus can be used to test protective anti-virus effects. In the experiments, potentiation of vaccine immunogenicity was tested using both an adjuvanted influenza vaccine (Fluad: as a control) and non-adjuvanted influenza vaccine (Agrippal, labeled simply "vaccine" in the Table below).

5 groups of 4 ferrets received control article or vaccine on SD 0 (vaccine) and 21 (boost). TA1 administration occurred as indicated in Table 5. The proposed thymosin dosage was deduced with reference to published data in mice and humans, and taking into account the weight of the ferret. A pre-bleeding checked the negativity of anti-influenza titer.

The vaccine (either Agrippal influPozzi seasonal vaccine, non-adjuvanted, or Fluad, MF-59 adjuvanted) was administered via intramuscular injection to the right leg at a full human dose of 0.5 mL. TA1 (0.285 or 0.570 mg/kg/dose) was administered by the subcutaneous route at a dose volume that, using a scaling factor for ferret/human dosing, corresponding to approximate human doses of 3.2 or 6.4 mg/kg. Animals were observed twice daily for mortality, general health, and both local and systemic signs of toxicity and illness as well as behavior under the responsibility of a professional veterinarian. Body weights were recorded prior to dosing only.

Figure 3:
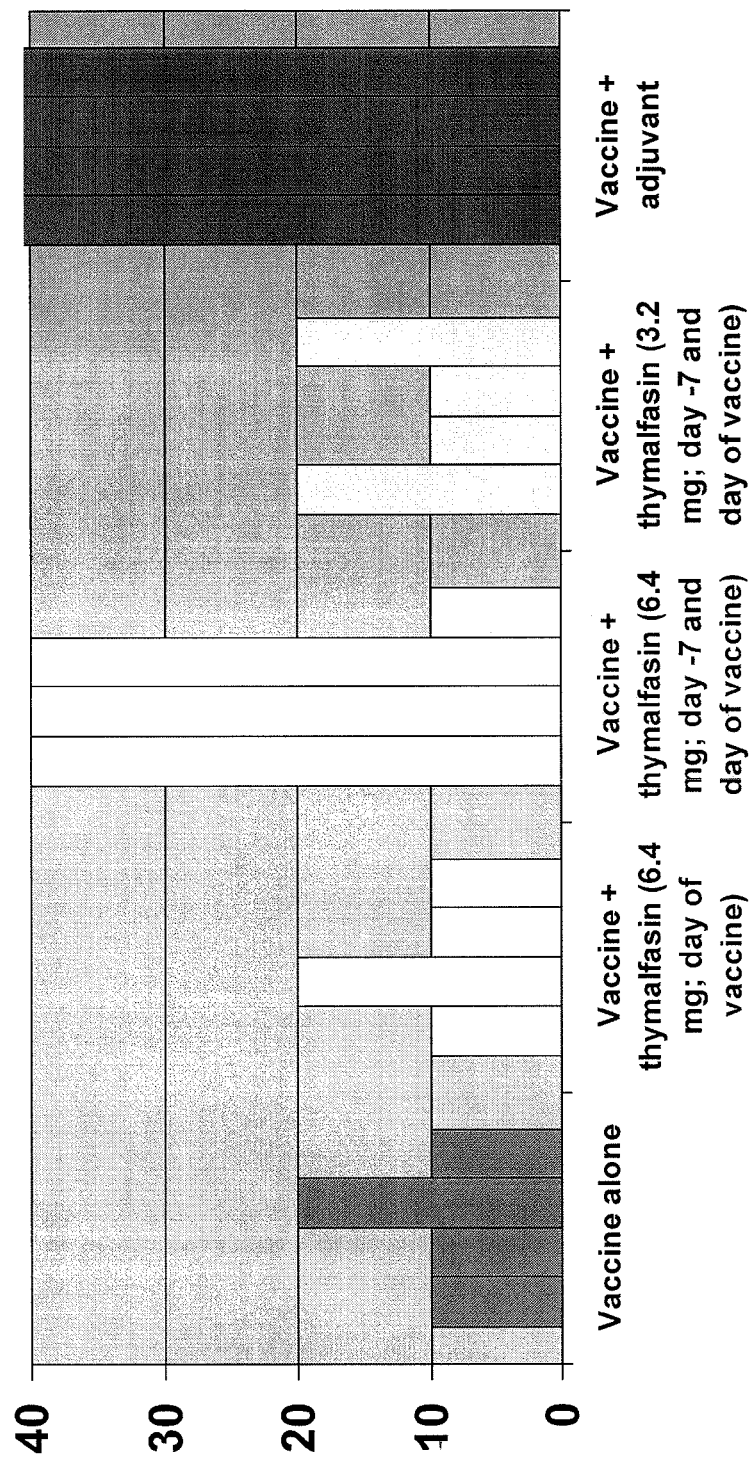
FIG. 3 shows the antibody titers achieved in ferrets with the human equivalent of 3.2 and 6.4 mg thymosin, when administered on the same day as an unadjuvanted vaccine, and in some cases seven days prior. An adjuvanted vaccine is shown as a positive control.

Blood samples for analysis of influenza antibody titer (hemagglutination-inhibition; HAI analysis) were collected from all the animals via a cardiac stick on SD 21 (prior to booster vaccine administration), SD 35, and SD 120. HAI analysis was performed in triplicate against the 3 vaccine strains (Florida [B], Brisbane 10 and Brisbane 59). Data for H1N1 N Brisbane 59 are shown in FIG. 3. All ferrets had pre-existing antibodies against the H3N2 N Brisbane 10.

TABLE 5

Study Design and Timeline

| Group (n = 4) | Treatments | TA1 Administrations | TA1 Dose (mg/kg) |
|---|---|---|---|
| 1 | Vaccine only | Not applicable - vaccine administered on SD 0 and 21 | — |
| 2 | Vaccine/TA1 | TA1 given 7 days before and at the same time as vaccine on SD 0 | 0.28 |
| 3 | Vaccine/TA1 | TA1 given 7 days before and at the same time as vaccine on SD 0 | 0.57 |
| 4 | Vaccine/TA1 | TA1 given at the same time as vaccine on SD 0 and 21 | 0.57 |
| 5 | Adjuvanted vaccine only | Not applicable - vaccine administered on SD 0 and 21 | — |

Results

HAI titer (Day 21) in ferrets was generally greater in animals receiving two injections of TA1 plus vaccine versus those receiving vaccine alone (see FIG. 3). A 0.57 mg/kg dose of TA1 (equivalent to a human dose of approximately 6.4 mg/kg) administered seven days prior to and on the day of vaccination was the best performing dose/schedule, as ¾ animals received desired anti-influenza antibodies with this regimen. The titer persisted when evaluated 42 days after vaccination. Similarly, ferrets receiving TA1 on day 0 and +21 showed higher HAI titer after vaccine booster than those boosted without TA1. The antibody response in ferrets receiving adjuvanted vaccine greatly exceeded that from non-adjuvanted vaccine, irrespective of TA1.

FIG. 3 shows the antibody titers in each group. A titer of 1:40 is considered protective. As shown, Thymalfasin at the human equivalent of 6.4 mg, given on day-7 and on the day of vaccination (without adjuvant), was protective. A 4-fold increase over vaccine alone was observed. Further, this dosing regimen produced protective titers in 3 of 4 animals.

TA1 appeared safe and well-tolerated, and no cage-side observations were noted. Thus, TA1 can enhance antibody response to non-adjuvanted influenza vaccine, a finding of relevance for vaccination of subjects with lowered response to vaccination, particularly the elderly Example 3

Enhancer of H1N1 Vaccination in Hemodialysis Patients

The ability of thymosin TA1 to enhance immune response to the MF59 adjuvanted H1N1 influenza monovalent vaccine, Focetria™ was investigated. The study was conducted in hemodialysis patients. Patients with end-stage renal disease requiring hemodialysis, or other conditions that compromise the immune system, as well as the elderly, often do not develop sufficient antibodies to fight off infectious disease such as H1N1 influenza. Additionally, many patients that achieve protective titers initially are unable to sustain these for longer periods of time, making them susceptible to infection and requiring revaccination or booster shots.

The randomized, three-arm study was conducted in approximately 120 patients with end-stage renal disease who are on chronic dialysis. One cohort of patients received the H1N1 vaccine only, while the other two groups received either two low-dose injections of thymalfasin (TA1) (3.2 mg seven days prior to vaccination and on the day of vaccination), or two higher dose injections of thymalfasin (6.4 mg seven days prior to vaccination and on the day of vaccination). All patients who did not achieve an antibody titer of at least 1:40 on day 21 received a second H1N1 vaccination on that day. Dosing regimens are based on preclinical results obtained in the ferret and mouse models. Blood was drawn at days 0, 21, 42, 84, and 168. A second dose of the H1N1 vaccine was administered to any patient who did not reach the protective titer at 18-28 days from the first vaccination (8 subjects, or 25%, of the 32 subjects receiving vaccine alone; 2, or 7.1% of the 28 subjects receiving vaccine and 3.2 mg doses of TA1; and 2, or 6.3%, of the 32 subjects receiving vaccine and 6.4 mg doses of TA1).

The primary efficacy endpoint for the study is the proportion of patients who achieve seroconversion, specifically, a significant rise in specific antibody titers believed to be protective. In the context of this study using HI titers, "seroconversion" is defined as a change from negative pre-vaccination serum (e.g., HI titer <1:10) to post-vaccination titer $\geq 1:40$ or at least a four-fold increase in titers from baseline. Additionally, patients will be followed for six months to assess the durability of the protective titers. "Seroprotection" is defined as an HI titer of $\geq 1:40$. The "Geometric Mean Ratio" (GMR) is the ratio of day x/day 1 geometric mean titers.

Thymalfasin treatment given with the H1N1 vaccine led to a highly statistical (p value $\leq 0.01$) increase in the percentage of subjects who seroconverted at 21 days after vaccination, when compared to those who received the H1N1 vaccine alone. Specifically, at 21 days following vaccination, 89% of patients in the low-dose arm achieved seroconversion as did 88% of patients in the high-dose arm, compared to only 56% of patients in the vaccine-only arm.

Figure 4:
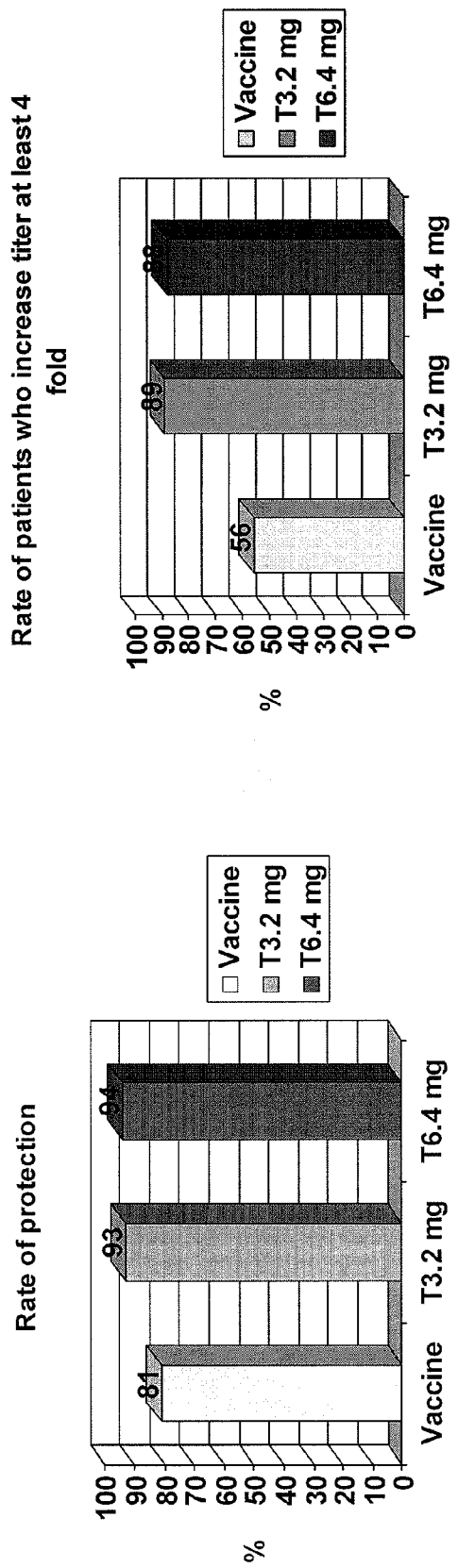
FIG. 4 shows results in patients with end-stage renal disease requiring hemodialysis. Patients received thymosin peptide on the day of vaccination (with Focetria™) and seven days prior. The left panel shows the percent of patients achieving seroprotection at day 21. The right panel shows the percent of patients achieving at least a four-fold increase in antibody titer at day 21.
Figure 5:
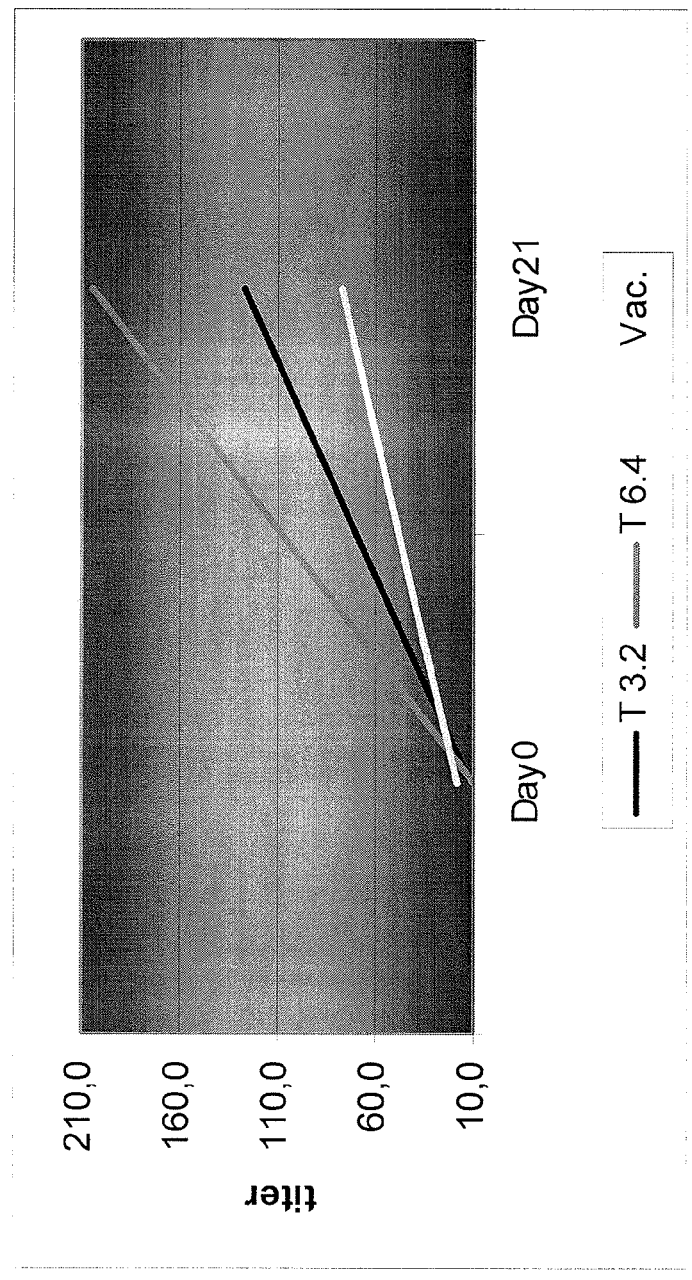
FIG. 5 shows the results in patients with end-stage renal disease requiring hemodialysis. Patients received thymosin peptide on the day of vaccination (with Focetria™) and seven days prior. The graph shows the development of antibody titers over the 21 day period following vaccination

As illustrated in FIG. 5 (showing mean titer at baseline and at day 21), treatment with two doses of thymalfasin increases the mean titer in a dose-dependent fashion. FIG. 4 shows that the number of persons with seroprotection and the number of persons who seroconvert are greater with thymalfasin treatment.

Thymanfasin treatment given with the H1N1 vaccine led to a statistically significant (P value=0.04) increase in the percentage of subjects who seroconverted, also when evaluated at 42 days after vaccination, compared to those who received the H1N1 vaccine alone. In addition, the improvement in titers seen in thymalfasin-treated patients was maintained at this timepoint. Specifically, when measured 42 days following vaccination, 93% of patients in the low-dose arm and 94% of patients in the high-dose arm achieved seroconversion, compared to only 77% of patients in the vaccine only arm of the study. This increased seroconversion compares favorably with that seen at 21 days following vaccination.

The following tables summarizes Micro neutralization (MN) and seroconversion (SC) data through day 84 of the study.

TABLE 6

Overall Population:

| CHMP criteria | V<br>N = 32 | V + T3.2<br>N = 28 | V + T6.4<br>N = 32 |
|---|---|---|---|
| Day 21 MN test | | | |
| Percent with SC | 21.9 | 25 | 31.6 |
| Percent with MN ≥ 1:20 | 50 | 46.4 | 62.5 |
| GMR | 2.23 | 1.95 | 2.46 |
| Day 42 MN test | | | |
| Percent with SC | 29 | 17.6 | 40.6 |
| Percent with MN ≥ 1:20 | 51.6 | 39.3 | 65.6 |
| | N = 31 | | |
| GMR | 2.27 | 1.72 | 2.33 |
| Day 84 MN test | | | |
| Percent with SC | 22.6 | 17.6 | 40 |
| Percent with MN ≥ 1:20 | 41.9 | 35.7 | 66.7 |
| | N = 31 | | N = 30 |
| GMR | 2.15 | 1.62 | 2.32 |

Seroconversion is defined as negative pre-vaccination serum (i.e., MN titer < 1:10) and post-vaccination MN titer ≥ 1:20 or a 4-fold increase from non negative (≥1:10) pre vaccination MN titer. GMR = ratios of day x/day 0 geometric mean MN titer.

Only Subjects who received 1 vaccine dose

| CHMP criteria | V<br>N = 26 | V + T3.2<br>N = 26 | V + T6.4<br>N = 30 |
|---|---|---|---|
| Day 21 MN test | | | |
| Percent with SC | 26.9 | 26.9 | 36.7 |
| Percent with MN ≥ 1:20 | 57.7 | 50 | 63.3 |
| GMR | 2.61 | 2.1 | 2.61 |
| Day 42 MN test | | | |
| Percent with SC | 32 | 15.4 | 43.3 |
| Percent with MN ≥ 1:20 | 56 | 42.3 | 66.7 |
| | N = 25 | | |
| GMR | 2.48 | 1.8 | 2.46 |
| Day 84 MN test | | | |
| Percent with SC | 24 | 19.2 | 42.9 |
| Percent with MN ≥ 1:20 | 44 | 38.5 | 67.9 |
| | N = 25 | | N = 28 |
| GMR | 2.25 | 1.68 | 2.42 |

Only Subjects non protected at the baseline:

| CHMP criteria | V<br>N = 25 | V + T3.2<br>N = 25 | V + T6.4<br>N = 27 |
|---|---|---|---|
| Day 21 MN test | | | |
| Percent with SC | 20 | 28 | 40.7 |
| Percent with MN ≥ 1:20 | 36 | 40 | 55.6 |
| GMR | 2.17 | 2.00 | 2.65 |
| Day 42 MN test | | | |
| Percent with SC | 28 | 20 | 44.4 |
| Percent with MN ≥ 1:20 | 40 | 32 | 59.3 |
| GMR | 2.33 | 1.74 | 2.42 |

TABLE 6-continued

| | | | |
|---|---|---|---|
| Day 84 MN test | | | |
| Percent with SC | 24 | 20 | 44 |
| Percent with MN ≥ 1:20 | 32 | 28 | 60 |
| | | | N = 25 |
| GMR | 2.36 | 1.62 | 2.40 |

Defined as negative pre-vaccination serum (i.e., MN titer < 1:10) or non negative (≥1:10) but non protected (i.e., MN titer ≤ 1:20)

Only Subjects negative at the baseline:

| CHMP criteria | V<br>N = 19 | V + T3.2<br>N = 18 | V + T6.4<br>N = 19 |
|---|---|---|---|
| Day 21 MN test | | | |
| Percent with MN ≥ 1:20 | 26.3 | 33.3 | 47.4 |
| GMR | 2.31 | 2.08 | 2.88 |
| Day 42 MN test | | | |
| Percent with MN ≥ 1:20 | 36.8 | 22.2 | 52.6 |
| GMR | 2.73 | 1.68 | 2.54 |
| Day 84 MN test | | | |
| Percent with MN ≥ 1:20 | 31.6 | 22.2 | 50 |
| | | | N = 18 |
| GMR | 2.88 | 1.71 | 2.42 |

Defined as negative pre-vaccination serum (i.e., MN titer < 1:10).

Only Subjects received 2 doses of vaccine:

| CHMP criteria | V<br>N = 6 | V + T3.2<br>N = 2 | V + T6.4<br>N = 2 |
|---|---|---|---|
| Day 21 MN test | | | |
| Percent with MN ≥ 1:20 | 16.7 | 0 | 50 |
| GMR | 1.12 | 1.00 | 1.00 |
| Day 42 MN test | | | |
| Percent with MN ≥ 1:20 | 33.3 | 0 | 50 |
| GMR | 1.59 | 1.00 | 1.00 |
| Day 84 MN test | | | |
| Percent with MN ≥ 1:20 | 33.3 | 0 | 50 |
| GMR | 1.78 | 1.00 | 1.19 |

Figure 6A:
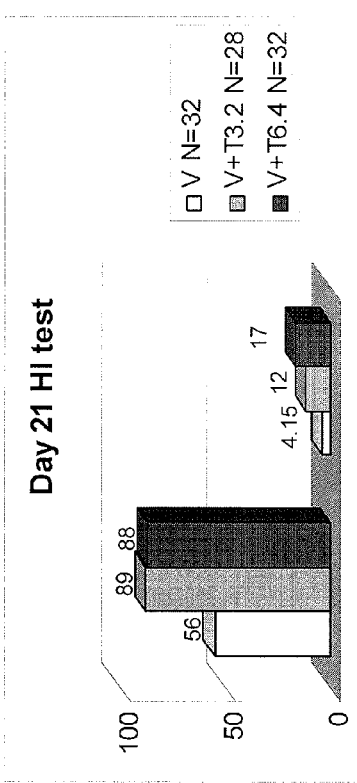
FIG. 6A shows results on Day 21.
Figure 6B:
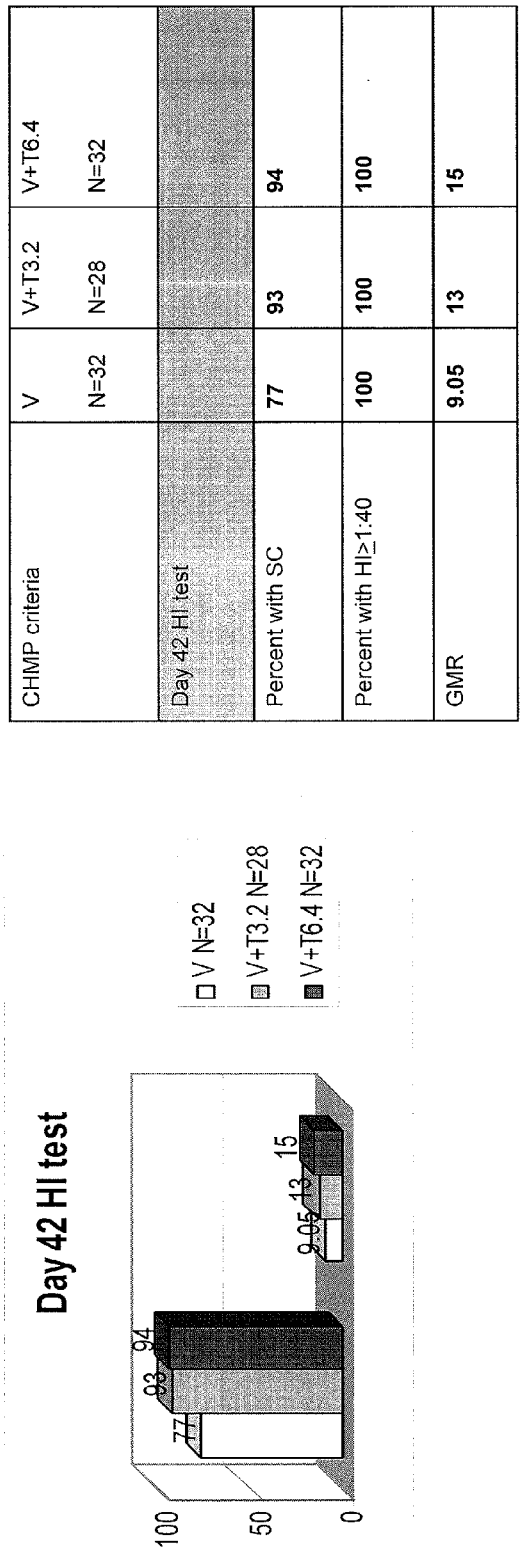
FIG. 6B shows results on day 42.
Figure 7A:
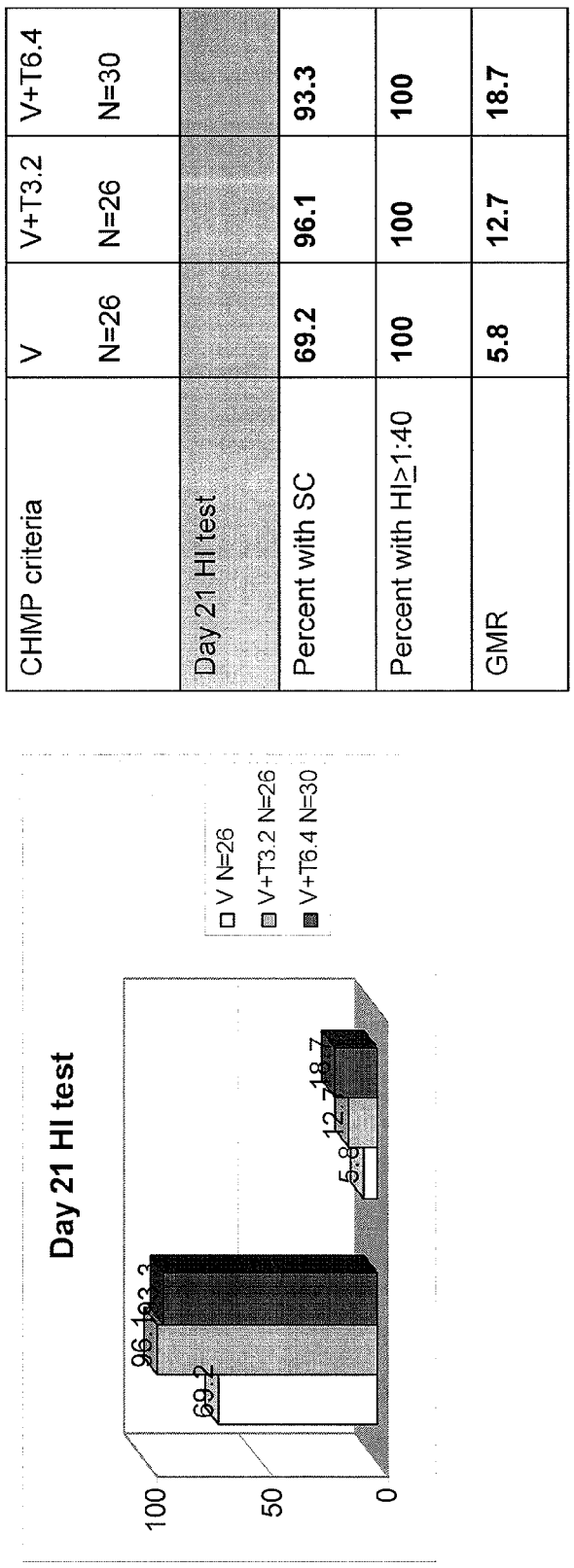
FIG. 7A shows results on Day 21.
Figure 7B:
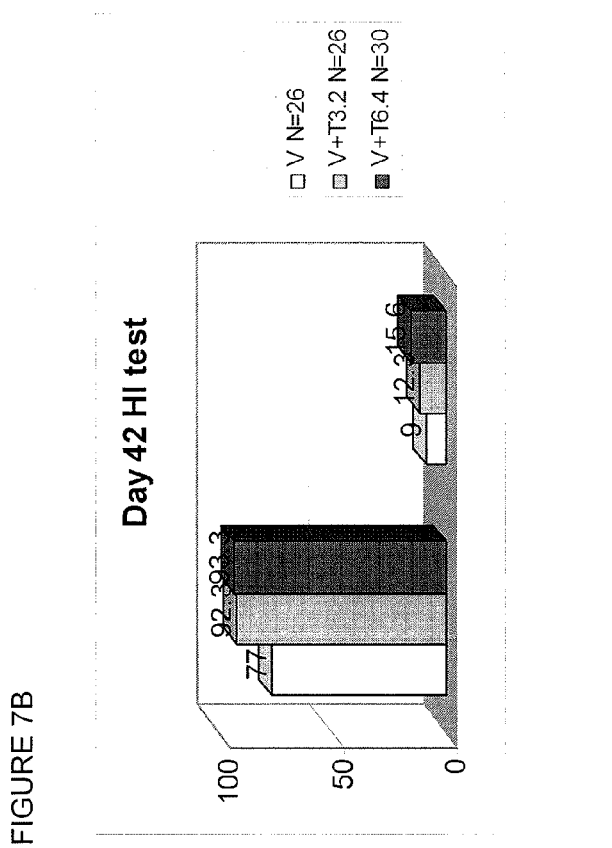
FIG. 7B shows results on day 42.
Figure 8A:
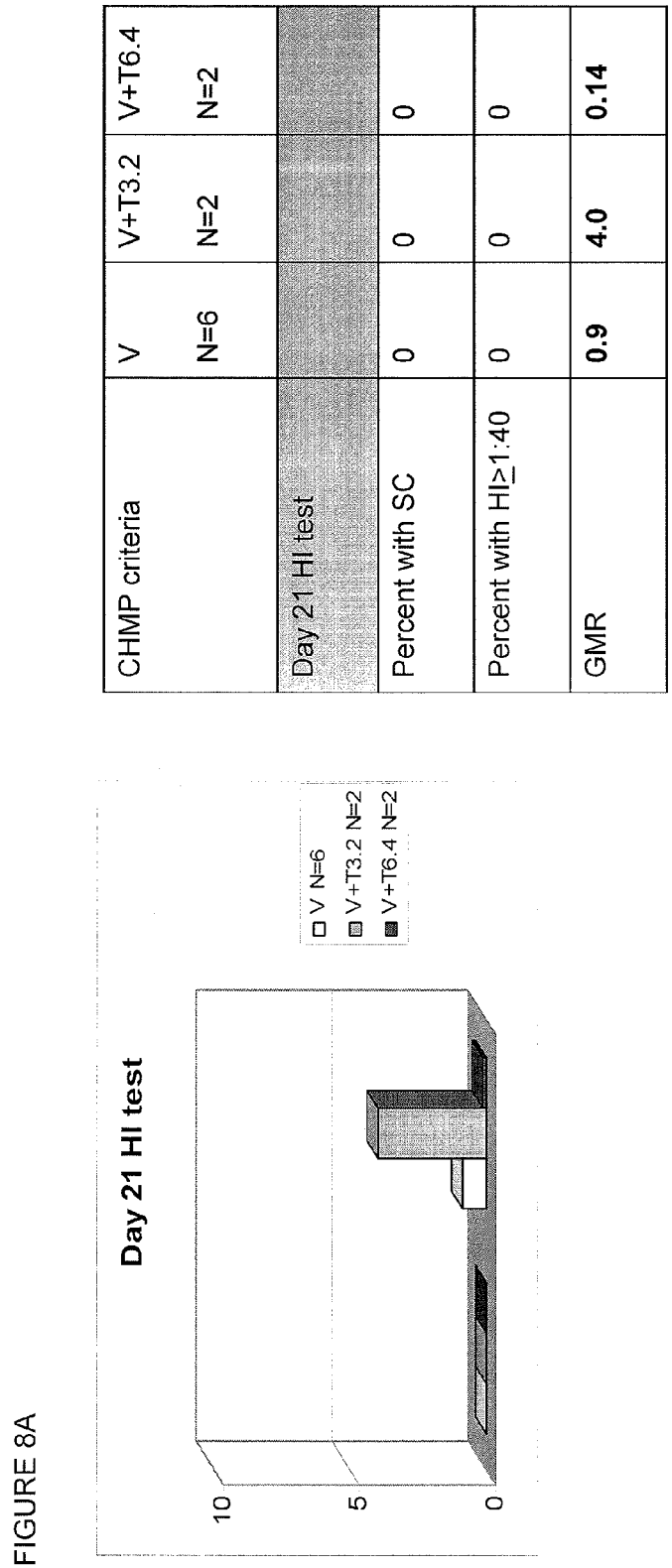
FIG. 8A shows results on Day 21.
Figure 8B:
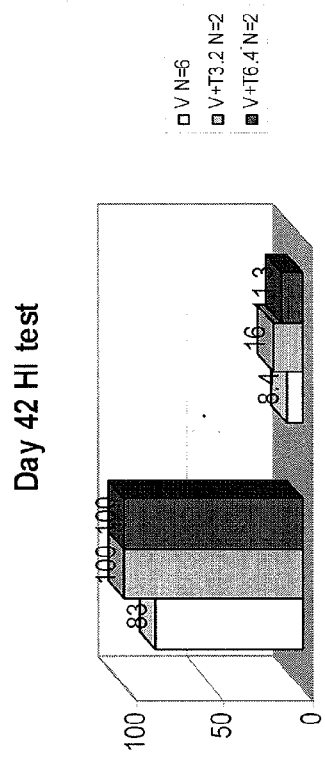
FIG. 8B shows results on day 42.

FIGS. 6 and 7 illustrate the results of HI test at days 21 and 42, and show a greater percent of patients with seroconversion and greater Geometric Mean Ratio with TA1 treatment. FIG. 8 illustrates the results for patients receiving a second vaccination, and shows the improvement with TA1 treatment at day 42.

Figure 9:
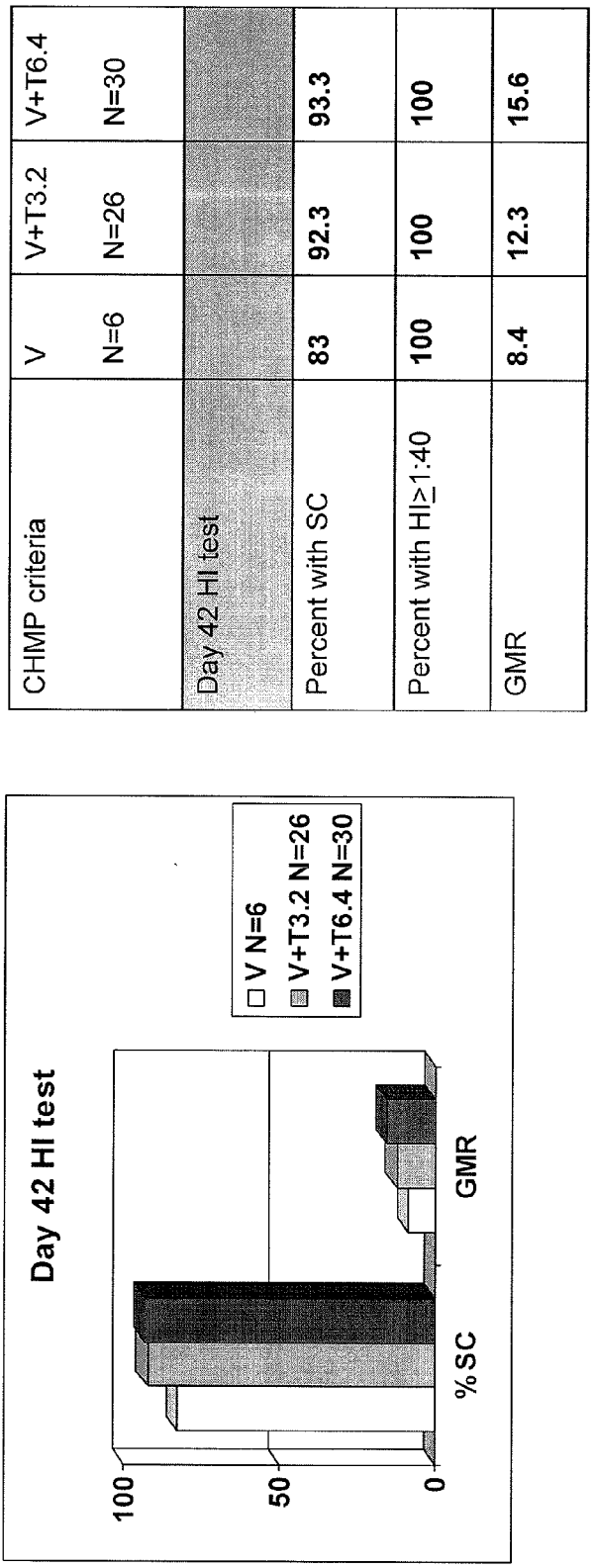
FIG. 9 shows percent seroconversion and geometric mean ratio (HI test) at day 42 in patients receiving two doses of influenza vaccine, as compared to patients receiving one vaccine dose and a two dose regimen of TA1.

FIG. 9 compares the results for patients receiving two doses of vaccine, with patients receiving one vaccination and TA1.

Figure 10A:
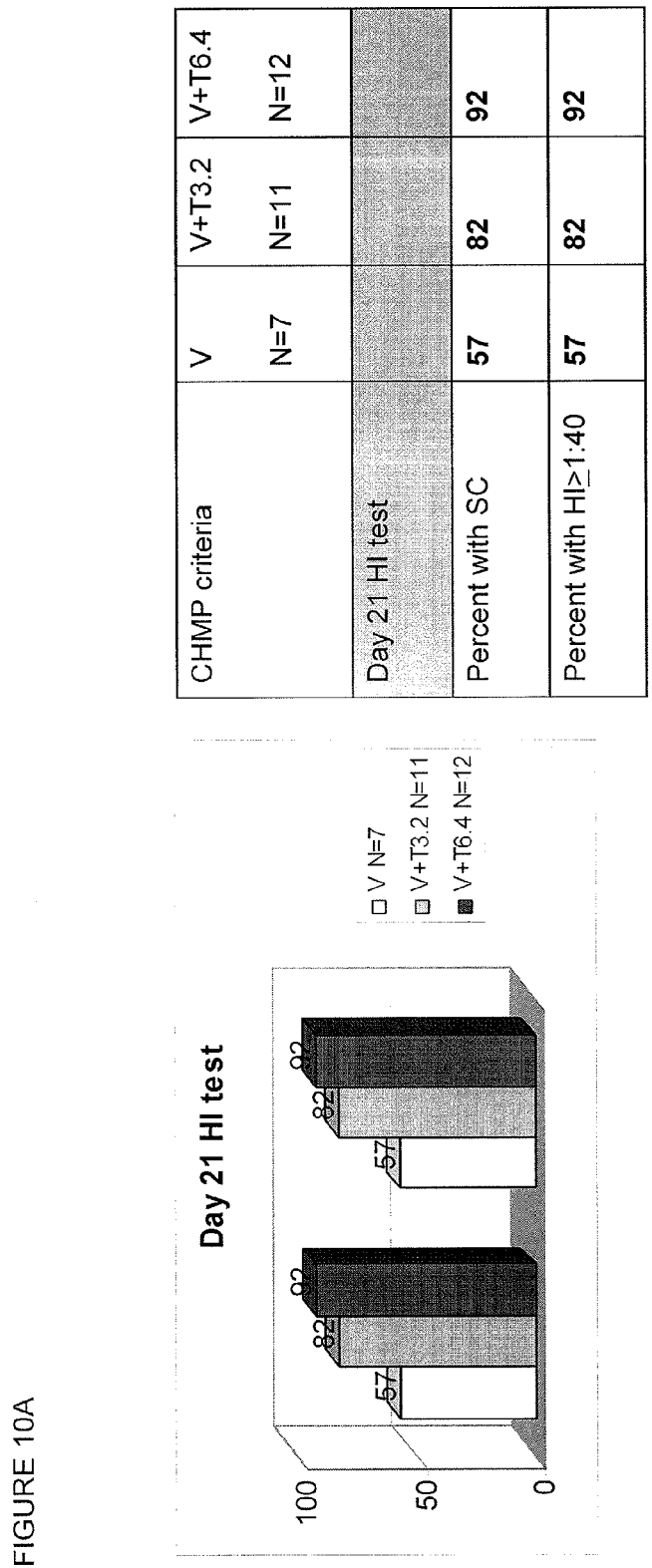
FIG. 10A shows results on Day 21.
Figure 10B:
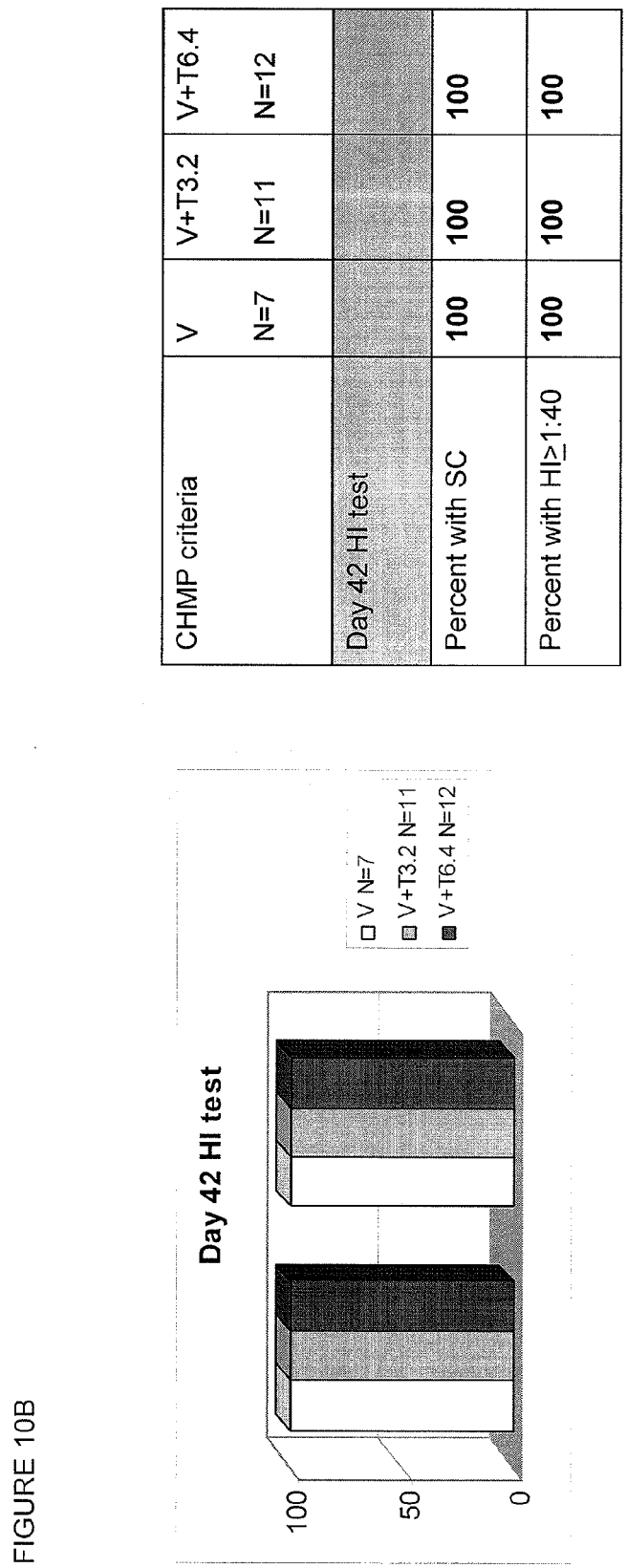
FIG. 10B shows results on day 42.
Figure 11:
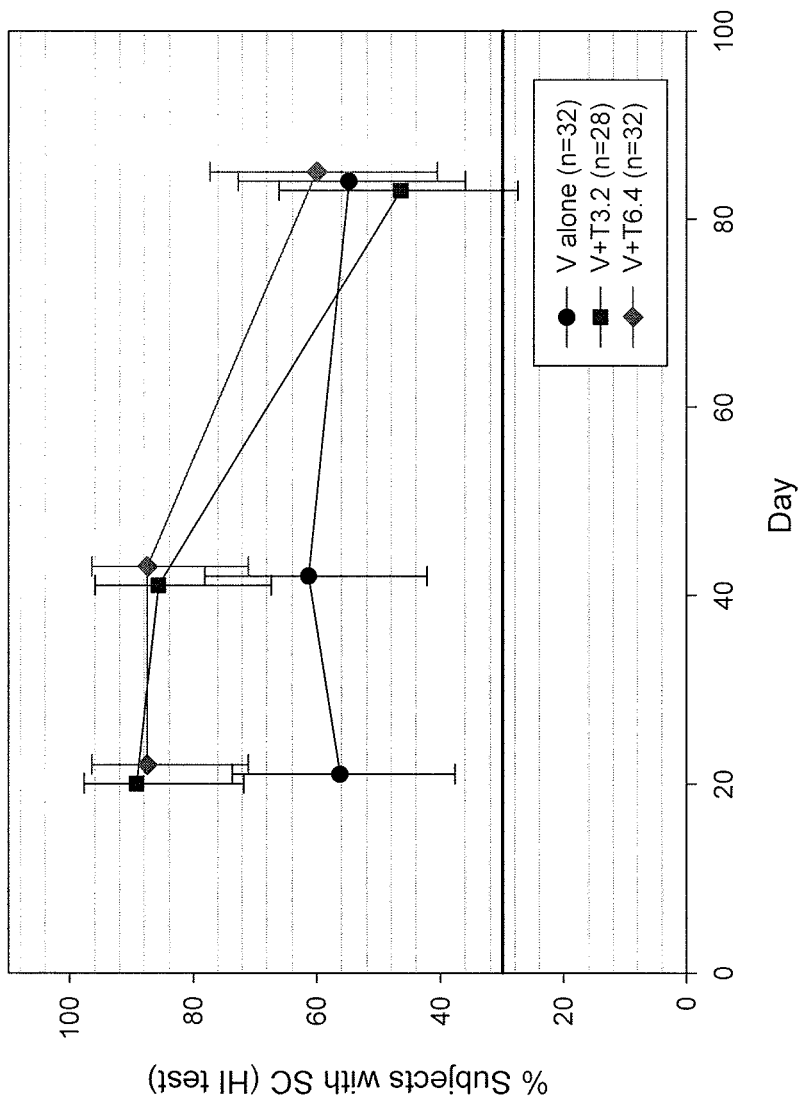
FIG. 11 shows seroconversion (HI test), with 95% confidence interval, in all patients over an 84 day period after influenza vaccination. For subjects receiving a second vaccination, the Day 21 titer was carried forward to Day 42 and 84.
Figure 12:
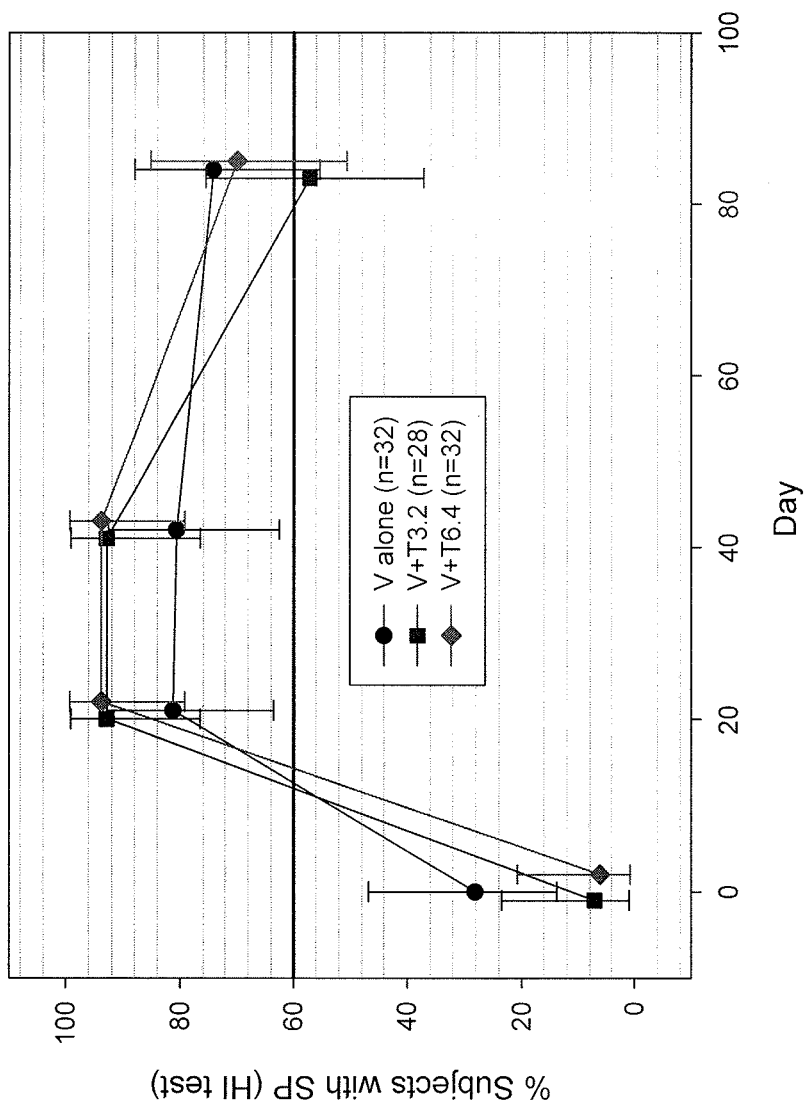
FIG. 12 shows seroprotection (HI test), with 95% confidence interval, in all patients over an 84 day period after influenza vaccination. For subjects receiving a second vaccination, the Day 21 titer was carried forward to Day 42 and 84.
Figure 13:
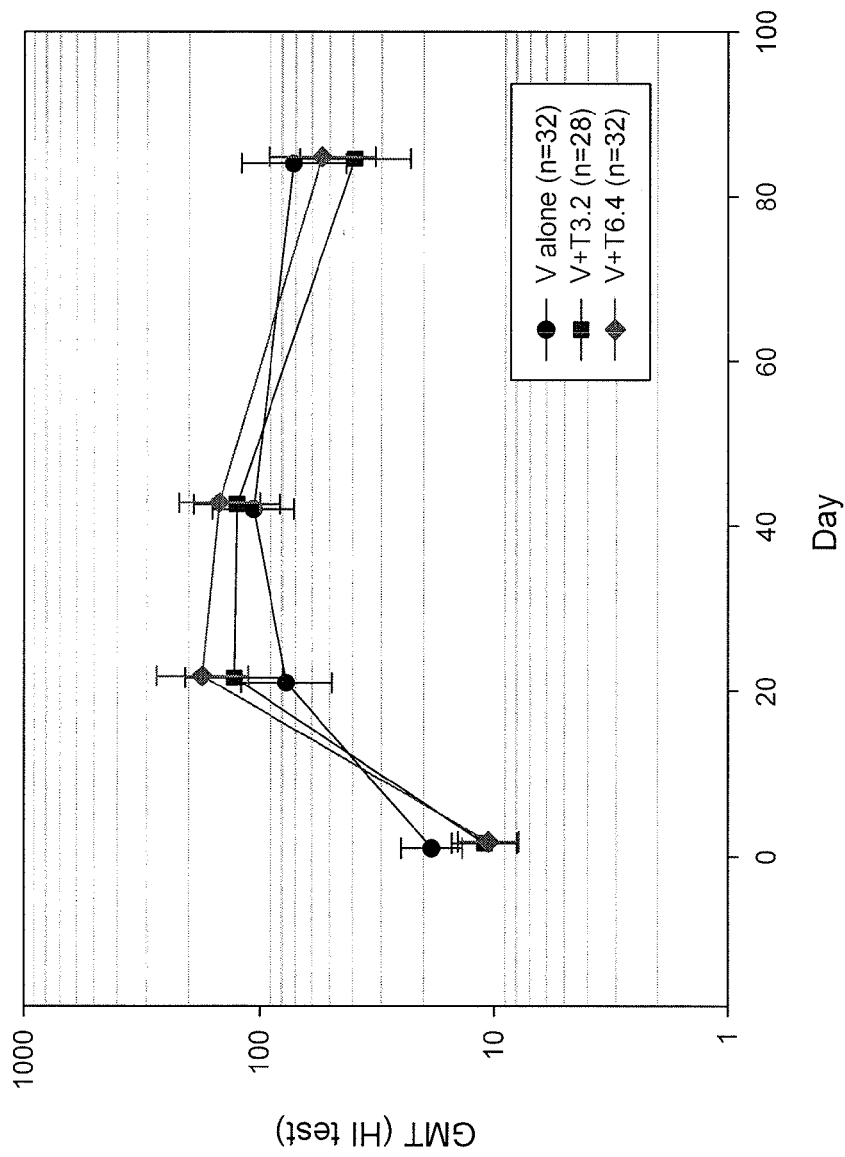
FIG. 13 shows Geometric Mean Titer (HI test), including 95% confidence interval, for all patients over an 84 day period after influenza vaccination. For subjects receiving a second vaccination, the Day 21 titer was carried forward to Day 42 and 84.
Figure 14:
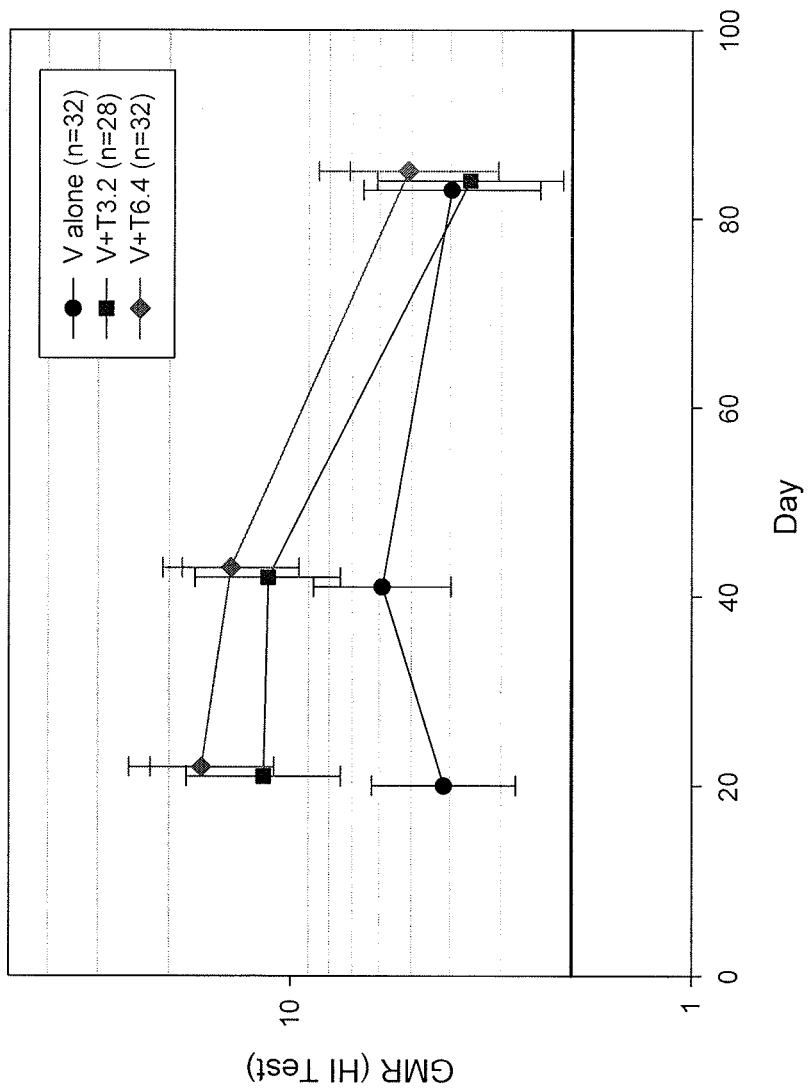
FIG. 14 shows Geometric Mean Ratio (HI test), including 95% confidence interval, for all patients over an 84 day period after influenza vaccination. For subjects receiving a second vaccination, the Day 21 titer was carried forward to Day 42 and 84.
Figure 15:
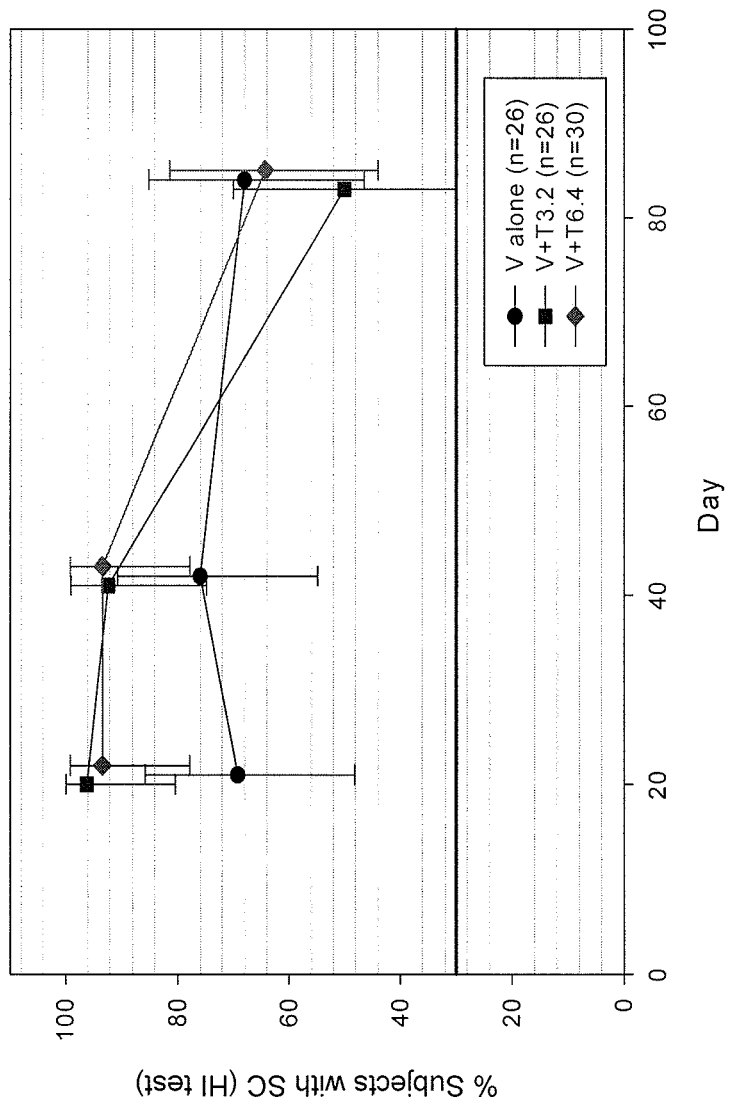
FIG. 15 shows seroconversion or significant increase (95% CI) in patients receiving only one influenza vaccination (HI test).
Figure 16:
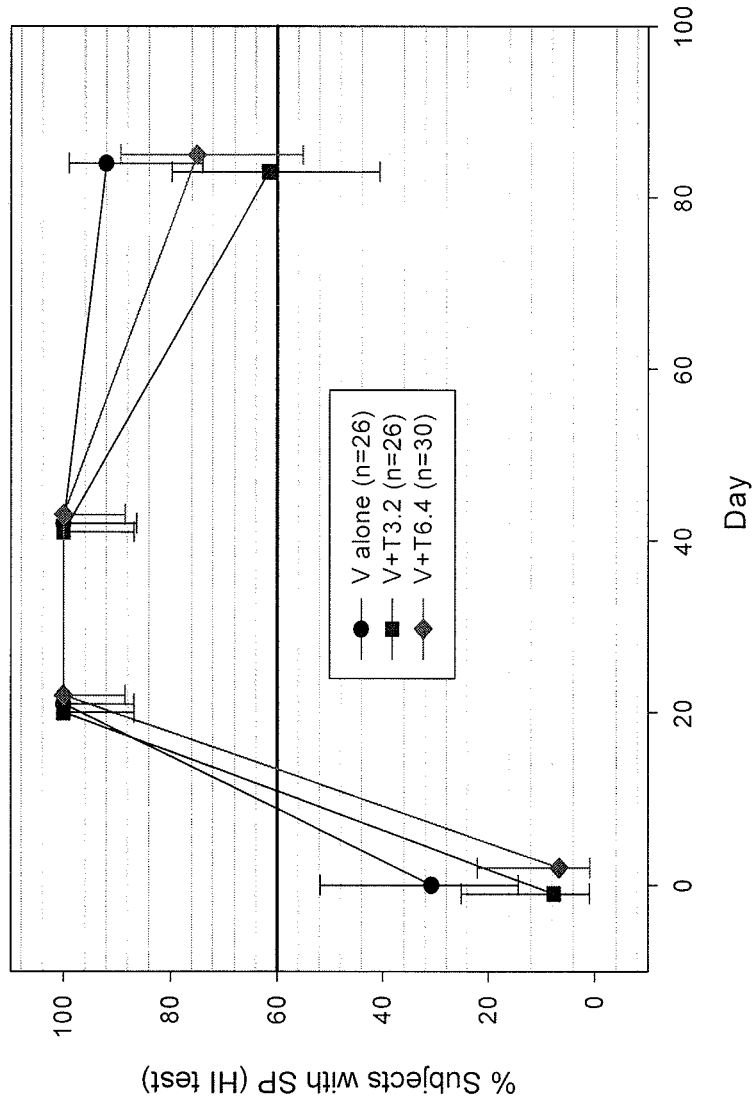
FIG. 16 shows seroprotection (95% CI) in patients receiving only one influenza vaccination (HI test).
Figure 17:
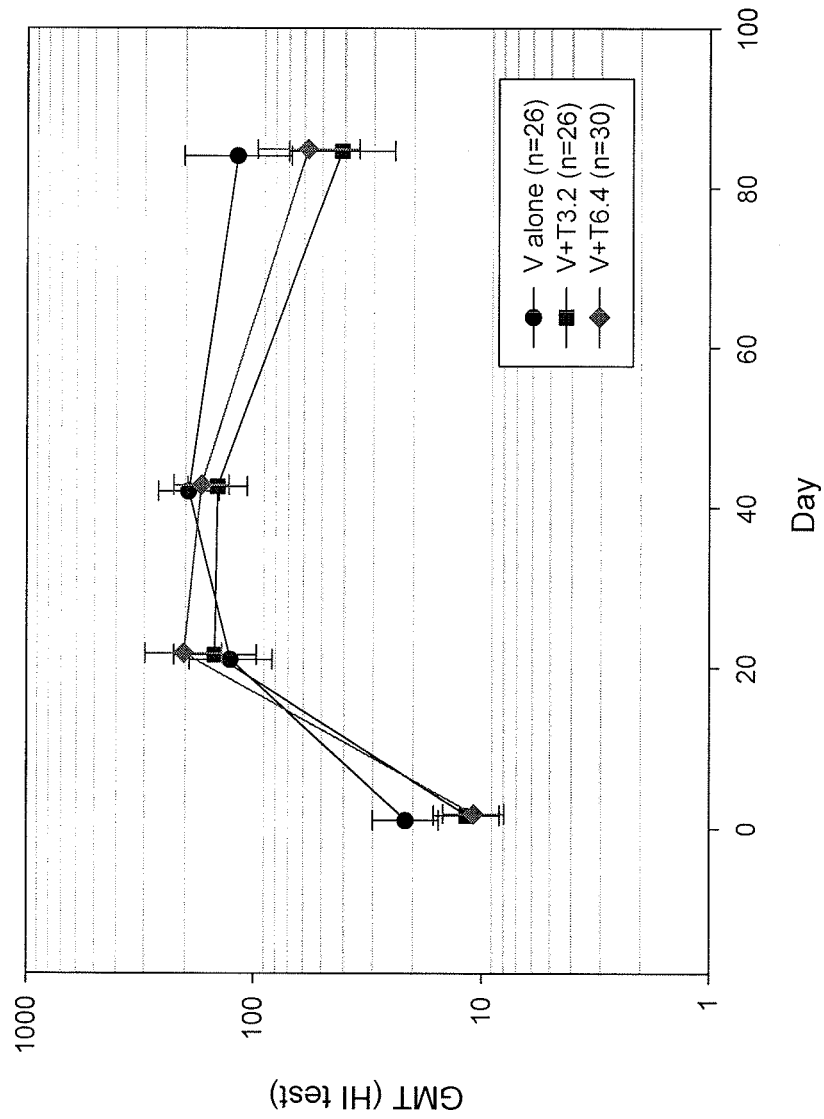
FIG. 17 shows Geometric Mean Titer (95% CI) in patients receiving only one influenza vaccination (HI test).
Figure 18:
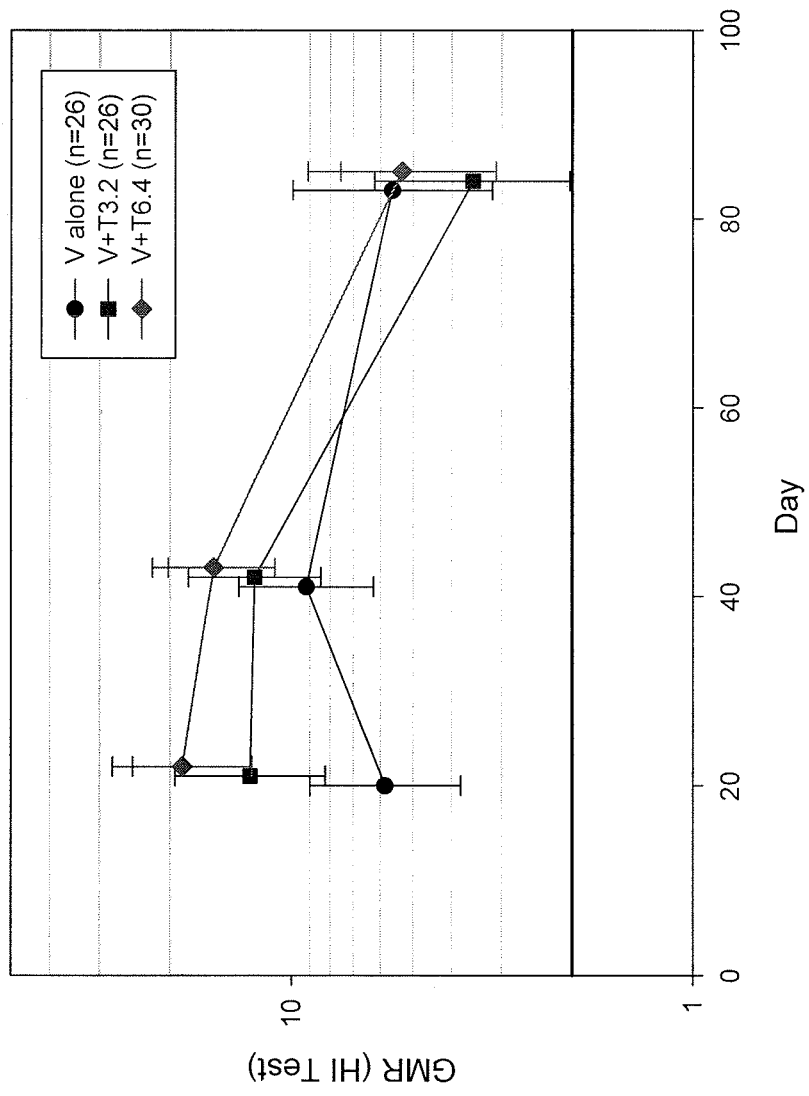
FIG. 18 shows Geometric Mean Ratio (95% CI) in patients receiving only one influenza vaccination (HI test).
Figure 19:
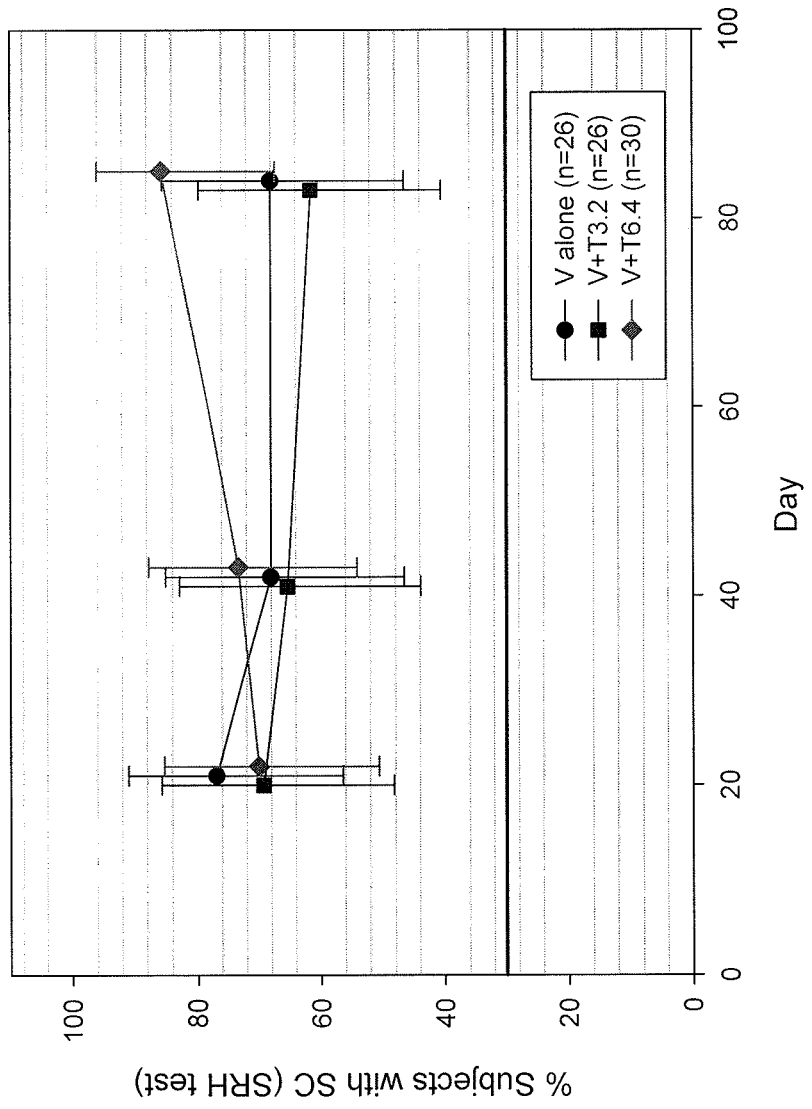
FIG. 19 shows seroconversion or significant increase (95% CI) in patients receiving only one influenza vaccination (SRH test).
Figure 20:
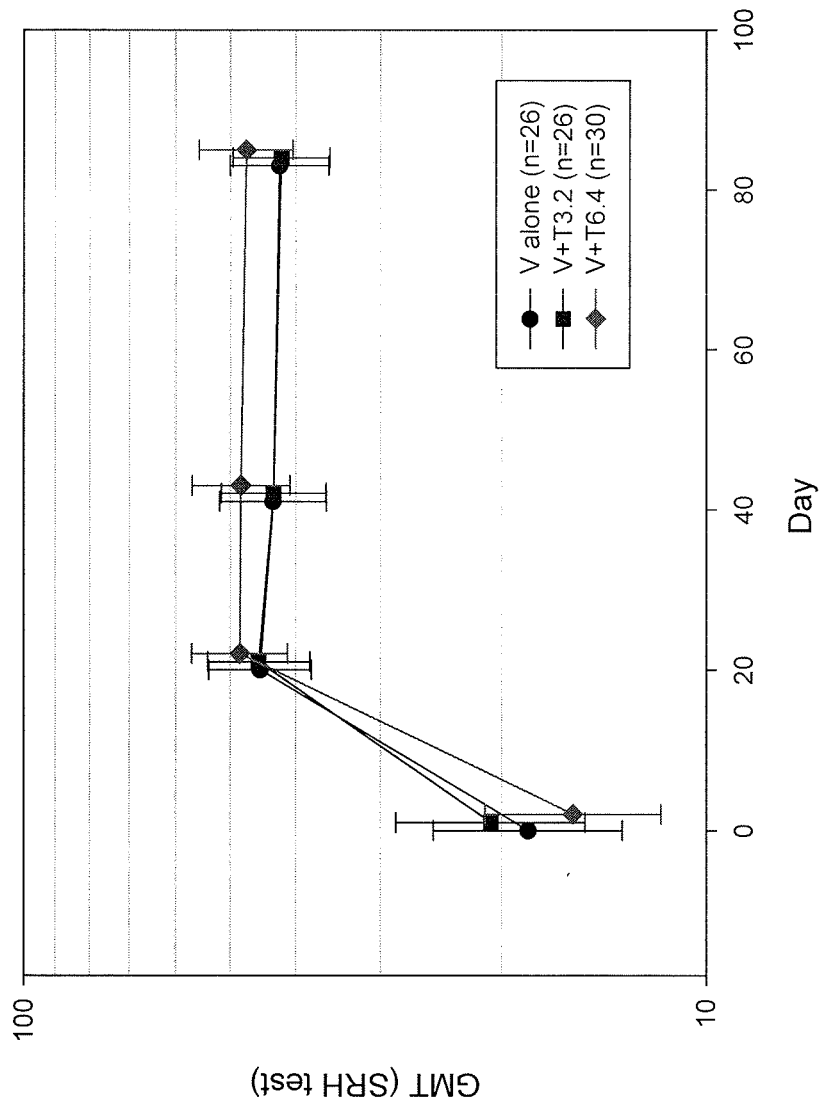
FIG. 20 shows Geometric Mean Area (95% CI) in patients receiving only one influenza vaccination (SHR test).
Figure 21:
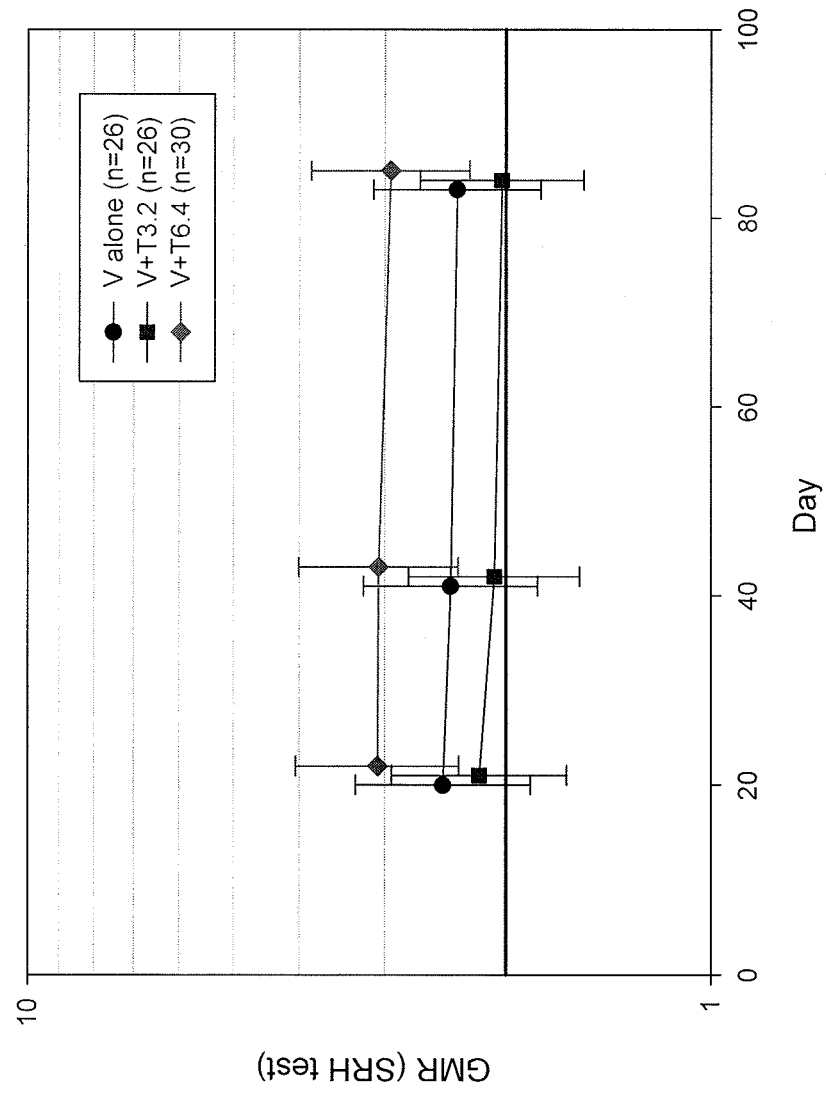
FIG. 21 shows Geometric Mean Ratio (95% CI) in patients receiving only one influenza vaccination.

FIG. 10 illustrates the results on day 21 and 42, for patients that were negative at baseline. While all patients achieved seroconversion by day 42, at day 21, patients receiving TA1 were more likely to have achieved seroconversion.

FIGS. 11 through 21 illustrate the results through day 84 of the study.

The study shows that two injections of TA1 given in addition to H1N1 adjuvanted vaccine led to an increase in vaccine efficacy, specifically: a more rapid response time, allowing patients to be protected sooner; as well as a better response than a single dose of vaccine alone or two vaccine injections.

The invention claimed is:

1. A method for vaccinating a subject, comprising, administering a vaccine to the subject, and administering thymosin peptide to the subject at a dose and regimen effective for providing higher antibody titers, speeding the development of antibody titers, and/or enhancing the duration of the antibody titers, with respect to administering the vaccine alone, wherein the thymosin peptide is administered from one to four times, with at least one dose administered prior to vaccine administration.

2. The method of claim 1, wherein he thymosin peptide is thymosin alpha 1 (TA1).

3. The method of claim 1, wherein the thymosin peptide is recombinant or synthetic.

4. The method of claim 1, wherein the thymosin peptide is pegylated.

5. The method of claim 1, wherein the subject is a mammal.

6. The method of claim 5, wherein the subject is a human.

7. The method of claim 5, wherein the subject is immunodeficient or refractory to vaccination.

8. The method of claim 7, wherein the subject is an elderly patient, or a patient on hemodialysis.

9. The method of claim 7, wherein the subject is an AIDS patient.

10. The method of claim 7, wherein the immunodeficiency is caused by a genetic defect, malnutrition, drug abuse, alcoholism, or cancer.

11. The method of claim 7, wherein the subject is undergoing treatment with an immunosuppressant drug.

12. The method of claim 1, wherein the vaccine comprises killed or inactivated infectious agents, or a tumor antigen.

13. The method of claim 1, wherein the vaccine is a DNA vaccine.

14. The method of claim 1, wherein the vaccine is a peptide subunit vaccine, recombinant vaccine, and/or toxoid vaccine.

15. The method of claim 1, wherein the vaccine comprises a virus vector or virus-like particles (VLPs).

16. The method of claim 1, wherein the vaccine is a live viral vaccine, live attenuated viral vaccine, or inactivated viral vaccine.

17. The method of claim 1 wherein the vaccine is a vaccine against an acute or chronic bacterial, viral, or parasitic infection.

18. The method of claim 17, wherein the vaccine is an influenza vaccine.

19. The method of claim 18, wherein the vaccine is against at least one influenza selected from H1N1, H1N8, H2N9, H3N8, H3N2, H4N6, H4N3, H5N3, H5N9, H5N1, H6N2, H6N8, H6N5, H6N1, H7N7, H7N1, H7N3, H8N4, H9N2, H9N6, H10N7, H10N8, H11N6, H11N9, H12N5, H13N6, H13N4,and/or H15N9.

20. The method of claim 17, wherein the vaccine is a hepatitis vaccine.

21. The method of claim 1, wherein the vaccine is a primary or secondary vaccination.

22. The method of claim 2, wherein the thymosin peptide is administered at a dosage of at least 0.5 mg of TA1 to a human patient.

23. The method of claim 22, wherein the thymosin peptide is administered at a dosage of 1 to 10 mg of TA1 to a human patient.

24. The method of claim 22, wherein the thymosin peptide is administered at a dosage of 3.2 or 6.4 mg of TA1 for a human patient.

25. The method of claim 1, wherein the thymosin peptide is administered by intramuscular or subcutaneous injection.

26. The method of claim 1, wherein the thymosin peptide is administered by continuous infusion.

27. The method of claim 1, wherein the thymosin peptide is administered from about one to ten days prior to vaccine administration.

28. The method of claim 1, wherein the thymosin peptide is administered twice.

29. The method of claim 1, wherein a booster vaccination is administered.

30. The method of claim 1, wherein the thymosin peptide is administered twice; a first time prior to administration of a primary vaccination, and a second time on the same day as the primary vaccination.

31. The method of claim 1, wherein the thymosin peptide is administered from about 5 to about 9 days prior to primary vaccination, and again on the day of primary vaccination.

32. The method of claim 31, wherein the thymosin peptide is administered about 7 days prior to primary vaccination and again on the day of primary vaccination.

33. The mehthod of claim 32, wherein the thymosin peptide is TA1 , and the vaccine is an influenza vaccine.

* * * * *